US012636493B2

(12) United States Patent (10) Patent No.: US 12,636,493 B2
Bittner et al. (45) Date of Patent: May 26, 2026

(54) NEUROSTIMULATION RESPONSE AND CONTROL

(71) Applicant: Medtronic, Inc., Minneapolis, MN (US)

(72) Inventors: Katie C. Bittner, White Bear Lake, MN (US); Sarah J. Offutt, Golden Valley, MN (US); Julia P. Slopsema, Minneapolis, MN (US); Leonid M. Litvak, Los Angeles, CA (US); Lance Zirpel, Lino Lakes, MN (US); Lisa M. Jungbauer Nikolas, Lino Lakes, MN (US); Katelynn M. Johnson, New Brighton, MN (US); Simeng Zhang, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 524 days.

(21) Appl. No.: 17/719,005

(22) Filed: Apr. 12, 2022

(65) Prior Publication Data

US 2022/0331589 A1 Oct. 20, 2022

Related U.S. Application Data

(60) Provisional application No. 63/246,592, filed on Sep. 21, 2021, provisional application No. 63/175,394, filed on Apr. 15, 2021.

(51) Int. Cl.
*A61N 1/36* (2006.01)
*A61N 1/05* (2006.01)
*G06N 20/00* (2019.01)
(52) U.S. Cl.
CPC ....... *A61N 1/36031* (2017.08); *A61N 1/0514* (2013.01); *G06N 20/00* (2019.01); *A61N 1/36007* (2013.01)

(58) Field of Classification Search
CPC .............. A61N 1/36031; A61N 1/0514; A61N 1/36139; A61N 1/36135; A61B 5/0205; A61B 5/395; A61B 5/7267; G06N 20/00
See application file for complete search history.

(56) References Cited

U.S. PATENT DOCUMENTS

| | | | |
|---|---|---|---|
| 3,902,501 A | 9/1975 | Citron et al. | |
| 4,407,303 A | 10/1983 | Åkerström | |

(Continued)

FOREIGN PATENT DOCUMENTS

| | | |
|---|---|---|
| CN | 103179899 A | 6/2013 |
| EP | 2465577 A1 | 6/2012 |

(Continued)

OTHER PUBLICATIONS

Apostolidis, "Neuromodulation for Intractable OAB", Neurourology and Urodynamics, vol. 30, No. 5, Jun. 9, 2011, pp. 66-770.

(Continued)

*Primary Examiner* — Michael W Kahelin
*Assistant Examiner* — Attiya Sayyada Hussaini
(74) *Attorney, Agent, or Firm* — Shumaker & Sieffert, P.A.

(57) ABSTRACT

An example method includes delivering one or more electrical stimulation signals to a patient, sensing a composite stimulation-evoked signal comprising a composite of signals generated by one or more signal sources in response to the one or more electrical stimulation signals, and controlling delivery of electrical stimulation therapy to the patient based on the composite stimulation-evoked signal.

23 Claims, 12 Drawing Sheets

(56)　　　　References Cited

U.S. PATENT DOCUMENTS

| 4,800,898 | A | | 1/1989 | Hess et al. |
| 4,811,742 | A | * | 3/1989 | Hassel ................... A61B 5/389 |
| | | | | 128/905 |
| 5,052,407 | A | | 10/1991 | Hauser et al. |
| 5,484,445 | A | | 1/1996 | Knuth |
| 5,702,429 | A | | 12/1997 | King |
| 5,957,965 | A | | 9/1999 | Moumane |
| 5,961,542 | A | | 10/1999 | Agarwala |
| 6,055,456 | A | | 4/2000 | Gerber |
| 6,104,960 | A | | 8/2000 | Duysens et al. |
| 7,174,215 | B2 | | 2/2007 | Bradley |
| 7,450,992 | B1 | | 11/2008 | Cameron |
| 7,463,928 | B2 | | 12/2008 | Lee et al. |
| 7,493,159 | B2 | | 2/2009 | Hrdlicka et al. |
| 7,519,429 | B2 | | 4/2009 | Sawan et al. |
| 7,979,119 | B2 | | 7/2011 | Kothandaraman et al. |
| 8,095,221 | B2 | | 1/2012 | Varrichio et al. |
| 8,180,461 | B2 | | 5/2012 | Mamo et al. |
| 8,233,991 | B2 | | 7/2012 | Woods et al. |
| 8,380,314 | B2 | | 2/2013 | Panken et al. |
| 8,412,335 | B2 | | 4/2013 | Gliner et al. |
| 8,597,183 | B2 | | 12/2013 | Addington et al. |
| 8,626,314 | B2 | | 1/2014 | Swoyer et al. |
| 8,840,550 | B2 | | 9/2014 | Addington et al. |
| 8,845,533 | B2 | | 9/2014 | Addington et al. |
| 8,886,326 | B2 | | 11/2014 | Alataris et al. |
| 8,918,184 | B1 | | 12/2014 | Torgerson et al. |
| 8,958,884 | B2 | | 2/2015 | Kothandaraman et al. |
| 8,983,627 | B2 | | 3/2015 | Pelger et al. |
| 9,042,990 | B2 | | 5/2015 | Carlson et al. |
| 9,126,043 | B2 | | 9/2015 | Kaula et al. |
| 9,220,890 | B2 | | 12/2015 | Alexander et al. |
| 9,248,288 | B2 | | 2/2016 | Panken et al. |
| 9,248,292 | B2 | | 2/2016 | Trier et al. |
| 9,302,113 | B2 | | 4/2016 | Ranu et al. |
| 9,314,616 | B2 | | 4/2016 | Wells et al. |
| 9,364,658 | B2 | | 6/2016 | Wechter |
| 9,381,356 | B2 | | 7/2016 | Parker et al. |
| 9,533,153 | B2 | | 1/2017 | Libbus et al. |
| 9,545,518 | B2 | | 1/2017 | Panken et al. |
| 9,555,246 | B2 | | 1/2017 | Jiang et al. |
| 9,561,372 | B2 | | 2/2017 | Jiang et al. |
| 9,643,010 | B2 | | 5/2017 | Ranu |
| 9,656,067 | B2 | | 5/2017 | Pelger et al. |
| 9,656,089 | B2 | | 5/2017 | Yip et al. |
| 9,713,706 | B2 | | 7/2017 | Gerber |
| 9,724,509 | B2 | | 8/2017 | Su et al. |
| 9,724,511 | B2 | | 8/2017 | Wei et al. |
| 9,782,122 | B1 | | 10/2017 | Pulliam et al. |
| 9,855,423 | B2 | | 1/2018 | Jiang et al. |
| 9,889,293 | B2 | | 2/2018 | Siegel et al. |
| 9,895,532 | B2 | | 2/2018 | Kaula et al. |
| 9,949,782 | B2 | | 4/2018 | Hagg et al. |
| 10,029,102 | B2 | | 7/2018 | Doan et al. |
| 10,076,667 | B2 | | 9/2018 | Kaula et al. |
| 10,080,899 | B2 | | 9/2018 | Rezai et al. |
| 10,092,762 | B2 | | 10/2018 | Jiang et al. |
| 10,105,542 | B2 | | 10/2018 | Jiang et al. |
| 10,124,171 | B2 | | 11/2018 | Kaula et al. |
| 10,201,702 | B2 | | 2/2019 | Bonde et al. |
| 10,213,604 | B2 | | 2/2019 | Dinsmoor et al. |
| 10,245,434 | B2 | | 4/2019 | Kaula et al. |
| 10,258,798 | B2 | | 4/2019 | Panken et al. |
| 10,376,704 | B2 | | 8/2019 | Mathur et al. |
| 10,406,369 | B2 | | 9/2019 | Jiang et al. |
| 10,478,619 | B2 | | 11/2019 | Lee et al. |
| 10,500,399 | B2 | | 12/2019 | Single |
| 10,569,088 | B2 | * | 2/2020 | Dinsmoor .......... A61N 1/36062 |
| 10,709,886 | B2 | | 7/2020 | Nagaoka et al. |
| 10,926,092 | B2 | | 2/2021 | Esteller et al. |
| 11,006,857 | B2 | | 5/2021 | Parker |
| 11,045,650 | B2 | | 6/2021 | Brink et al. |
| 11,129,991 | B2 | | 9/2021 | Dinsmoor et al. |
| 11,305,123 | B2 | | 4/2022 | Steinke |
| 11,493,473 | B2 | | 11/2022 | Beaty et al. |
| 11,524,163 | B2 | | 12/2022 | Baynham et al. |
| 11,633,602 | B2 | | 4/2023 | Single et al. |
| 11,745,015 | B2 | | 9/2023 | Stubbs et al. |
| 11,801,384 | B2 | | 10/2023 | Brannon et al. |
| 11,944,820 | B2 | | 4/2024 | Parker et al. |
| 11,998,747 | B2 | | 6/2024 | Stubbs et al. |
| 12,023,505 | B2 | | 7/2024 | Zhang et al. |
| 12,303,692 | B2 | | 5/2025 | Stanslaski et al. |
| 12,303,695 | B2 | | 5/2025 | Baynham et al. |
| 2003/0045919 | A1 | | 3/2003 | Swoyer et al. |
| 2005/0245993 | A1 | | 11/2005 | Varrichio et al. |
| 2006/0224187 | A1 | | 10/2006 | Bradley et al. |
| 2007/0100388 | A1 | | 5/2007 | Gerber |
| 2007/0100408 | A1 | | 5/2007 | Gerber et al. |
| 2008/0269740 | A1 | | 10/2008 | Bonde et al. |
| 2008/0288020 | A1 | * | 11/2008 | Einav ................. A61N 1/36003 |
| | | | | 607/48 |
| 2010/0030227 | A1 | | 2/2010 | Kast et al. |
| 2010/0280579 | A1 | * | 11/2010 | Denison ................. G16H 50/30 |
| | | | | 607/62 |
| 2010/0324570 | A1 | | 12/2010 | Rooney et al. |
| 2011/0313488 | A1 | | 12/2011 | Hincapie Ordonez et al. |
| 2013/0317567 | A1 | | 11/2013 | Vallapureddy et al. |
| 2014/0243926 | A1 | | 8/2014 | Carcieri |
| 2015/0088025 | A1 | * | 3/2015 | Litvak ................... A61B 5/316 |
| | | | | 600/546 |
| 2016/0045747 | A1 | | 2/2016 | Jiang et al. |
| 2016/0303376 | A1 | * | 10/2016 | Dinsmoor .......... A61N 1/36139 |
| 2016/0339259 | A1 | | 11/2016 | Davis et al. |
| 2016/0361535 | A1 | | 12/2016 | Perryman et al. |
| 2017/0239470 | A1 | | 8/2017 | Wei et al. |
| 2017/0298346 | A9 | | 10/2017 | Carter et al. |
| 2017/0304608 | A1 | | 10/2017 | Swoyer et al. |
| 2017/0333698 | A1 | | 11/2017 | Gerber et al. |
| 2018/0110987 | A1 | | 4/2018 | Parker |
| 2018/0132760 | A1 | | 5/2018 | Parker |
| 2018/0154144 | A1 | | 6/2018 | Brink et al. |
| 2018/0214691 | A1 | | 8/2018 | Famm et al. |
| 2018/0228547 | A1 | | 8/2018 | Parker et al. |
| 2018/0304075 | A1 | * | 10/2018 | Su ....................... A61N 1/36132 |
| 2019/0060634 | A1 | | 2/2019 | Skubitz et al. |
| 2019/0060636 | A1 | | 2/2019 | Steigauf et al. |
| 2019/0060647 | A1 | | 2/2019 | Su et al. |
| 2019/0099601 | A1 | | 4/2019 | Torgerson |
| 2019/0133522 | A1 | * | 5/2019 | Scott ................... A61B 5/4041 |
| 2019/0151658 | A1 | | 5/2019 | Jia et al. |
| 2019/0151659 | A1 | | 5/2019 | Mishra et al. |
| 2019/0183526 | A1 | | 6/2019 | Tranchina et al. |
| 2019/0255331 | A1 | | 8/2019 | Subbaroyan |
| 2019/0255333 | A1 | | 8/2019 | Baru et al. |
| 2019/0255339 | A1 | | 8/2019 | Lee et al. |
| 2019/0269924 | A1 | | 9/2019 | Su et al. |
| 2019/0282818 | A1 | | 9/2019 | Bonde et al. |
| 2019/0351244 | A1 | | 11/2019 | Shishilla et al. |
| 2019/0388692 | A1 | * | 12/2019 | Dinsmoor .......... A61N 1/36139 |
| 2019/0388695 | A1 | | 12/2019 | Dinsmoor et al. |
| 2020/0009367 | A1 | | 1/2020 | Huertas Fernandez et al. |
| 2020/0046980 | A1 | | 2/2020 | Moffitt et al. |
| 2020/0139115 | A1 | | 5/2020 | Verity |
| 2020/0139138 | A1 | | 5/2020 | Sit et al. |
| 2020/0147375 | A1 | | 5/2020 | Su et al. |
| 2020/0171313 | A1 | | 6/2020 | Dinsmoor et al. |
| 2020/0306528 | A1 | | 10/2020 | Linden et al. |
| 2020/0323462 | A1 | | 10/2020 | Jiang et al. |
| 2020/0338267 | A1 | | 10/2020 | Gerber et al. |
| 2020/0353257 | A1 | | 11/2020 | Bennett et al. |
| 2020/0397361 | A1 | | 12/2020 | Nelson et al. |
| 2021/0016091 | A1 | | 1/2021 | Parker et al. |
| 2021/0031032 | A1 | | 2/2021 | Zirpel et al. |
| 2021/0121696 | A1 | | 4/2021 | Parker et al. |
| 2021/0361942 | A1 | | 11/2021 | Su et al. |
| 2022/0000548 | A1 | | 1/2022 | Mickelsen |
| 2022/0331589 | A1 | | 10/2022 | Bittner et al. |
| 2022/0355115 | A1 | | 11/2022 | Moore et al. |
| 2023/0355978 | A1 | | 11/2023 | Fernandez et al. |
| 2024/0091539 | A1 | | 3/2024 | Dinsmoor et al. |
| 2024/0350804 | A1 | | 10/2024 | Grill et al. |
| 2024/0399153 | A1 | | 12/2024 | Stubbs et al. |

(56) References Cited

U.S. PATENT DOCUMENTS

| | | |
|---|---|---|
| 2025/0041605 A1 | 2/2025 | Steinke et al. |
| 2025/0114612 A1 | 4/2025 | Williams et al. |
| 2025/0135210 A1 | 5/2025 | Hoffer et al. |

FOREIGN PATENT DOCUMENTS

| | | | |
|---|---|---|---|
| EP | 2029220 B1 | 1/2013 | |
| EP | 2605701 A1 | 6/2013 | |
| EP | 3180072 B1 | 11/2018 | |
| EP | 2870979 B1 | 2/2021 | |
| WO | 1998020933 | 5/1998 | |
| WO | 2007136266 A1 | 11/2007 | |
| WO | 2012021976 A1 | 2/2012 | |
| WO | 2014201454 A2 | 12/2014 | |
| WO | WO-2019204884 A1 * | 10/2019 | .............. A61B 5/24 |
| WO | 2019232544 A1 | 12/2019 | |
| WO | 2020243104 A1 | 12/2020 | |
| WO | 2021016616 A2 | 1/2021 | |
| WO | 2025027452 A1 | 2/2025 | |
| WO | 2025118038 A1 | 6/2025 | |

OTHER PUBLICATIONS

Blok et al., "Programming settings and recharge interval in a prospective study of a rechargeable sacral neuromodulation system for the treatment of overactive bladder", Neurourology and Urodynamics, vol. 37, 2018, pp. S17-S22, (Applicant points out, in accordance with MPEP 609.04(a), that the year of publication, 2018, is sufficiently earlier than the effective U.S. filing date, so that the particular month of publication is not an issue.).

Chai et al., "Modified techniques of S3 foramen localization and lead implantation in S3 neuromodulation", Surgical Techniques In Urology, vol. 58, Nov. 2001, p. 786-790.

Daneshgari, "Applications of Neuromodulation of the Lower Urinary Tract in Female Urology", International Braz J Urol, vol. 32, No. 3, Jun. 2006, pp. 262-272.

Dr. Stephen Cohen, "Pelvic Nerves", Standard of Care, Dec. 26, 2020, 5 pp.

Hellström et al., "Sacral nerve stimulation lead implantation using the o-arm", BMC Urology, vol. 13, No. 48, Oct. 16, 2013, 5 pp.

Hetzer et al., "New screening technique for sacral nerve stimulation under local anaesthesia", Tech Coloproctol, vol. 9, Apr. 2005, p. 25-28.

Hetzer, "Fifteen years of sacral nerve stimulation: from an open procedure to a minimally invasive technique", Colorectal Disease, vol. 13, No. S2, Feb. 1, 2011, pp. 1-4.

International Search Report and Written Opinion of International Application No. PCT/US2022/024378 dated Jul. 14, 2022, p. 13.

Kessler et al., "Prolonged Sacral Neuromodulation Testing Using Permanent Leads: A More Reliable Patient Selection Method", European Urology, vol. 47, No. 5, May 2005, pp. 660-665.

Malaguti, "Interventional neurophysiology and an implantable system for neurostimulation of the sacral area", Functional Neurology, vol. 24, No. 4, Oct. 1, 2009, pp. 207-219.

Marcelissen et al., "New developments in sacral neuromodulation for lower urinary tract dysfunction", Maastricht University, 2011, 155 pp., (Applicant points out, in accordance with MPEP 609.04(a), that the year of publication, 2011, is sufficiently earlier than the effective U.S. filing date, so that the particular month of publication is not an issue.).

Matzel et al., "Sacral Neuromodulation: Standardized Electrode Placement Technique", Neuromodulation: Technology at the Neural Interface, vol. 20, No. 8, 2018, pp. 816-824, (Applicant points out, in accordance with MPEP 609.04(a), that the year of publication, 2018, is sufficiently earlier than the effective U.S. filing date, so that the particular month of publication is not an issue.).

Medtronic, Inc., "InterStim Therapy: Model 3093 Lead, Model 3889 Lead", Feb. 1, 2018, 34 pp.

Medtronic, Inc., "Interstim Therapy: Model 3095 Quadripolar Extension", Implant Manual, 2014, 16 pp., (Applicant points out, in accordance with MPEP 609.04(a), that the year of publication, 2014, is sufficiently earlier than the effective U.S. filing date, so that the particular month of publication is not an issue.).

Medtronic, Inc., "Medtronic Sacral Neuromodulation Therapy (Interstim)", System Overview and Compatibility Insert, May 30, 2018, 10 pp.

Peters et al., "Sacral Versus Pudendal Nerve Stimulation for Voiding Dysfunction: A Prospective, Single-Blinded, Randomized, Crossover Trial", Neurourology and Urodynamics, vol. 24, No. 7, Sep. 21, 2005, pp. 643-647.

Siegel et al., "Management of voiding dysfunction with an implantable neuroprosthesis", Urologogic Clinics of North America, vol. 19, No. 1, Feb. 1, 1992, pp. 163-170.

Spinelli et al., "Latest Technologic and Surgical Developments in Using InterStim™ Therapy for Sacral Neuromodulation: Impact on Treatment Success and Safety", European Urology, vol. 54, No. 6, Dec. 2008, pp. 1287-1296.

Spinelli et al., "New sacral neuromodulation lead for percutaneous implantation using local anesthesia: description and first experience", The Journal of Urology, vol. 170, No. 5, Nov. 2003, pp. 1905-1907.

Sun et al., "Closed-loop Neurostimulation: The Clinical Experience", Neurotherapeutics, vol. 11, May 22, 2014, p. 553-563.

Sutherland et al., "Sacral Nerve Stimulation for Voiding Dysfunction: One Institution's 11-Year Experience", Neurourology and Urodynamics, vol. 26, Oct. 31, 2006, pp. 19-28.

U.S. Appl. No. 17/658,978, filed Apr. 12, 2022, naming inventors Offutt et al.

U.S. Appl. No. 17/658,984, filed Apr. 12, 2022, naming inventors Offutt et al.

Wei et al., "Functional Electrical Stimulation as a Neuroprosthesis to Treat Urinary Incontinence", 5th International IEEE/EMBS Conference on Neural Engineering, Apr. 27, 2011, pp. 650-654.

Williams et al., "Procedural Techniques in Sacral Nerve Modulation", International Urogynecology Journal, vol. 21, Oct. 23, 2010, Page pp. 453-460.

Wöllner et al., "Sacral neuromodulation", BJU International, vol. 110, No. 1, Jun. 12, 2012, pp. 146-159.

Zhang et al., "Remotely programmed sacral neuromodulation for the treatment of patients with refractory overactive bladder: a prospective randomized controlled trial evaluating the safety and efficacy of a novel sacral neuromodulation device", World Journal of Urology, vol. 37, Feb. 26, 2019, p. 2481-2492.

Communication pursuant to Article 94(3) EPC from counterpart European Application No. 22721545.6 dated Dec. 26, 2025, 4 PP.

* cited by examiner

452

DELIVER ELECTRIC STIMULATION WAVEFORM TO A PATIENT

454

SENSE COMPOSITE STIMULATION-EVOKED SIGNAL IN RESPONSE TO ELECTRIC STIMULATION

456

CONTROL DELIVERY OF ELECTRIC STIMULATION THERAPY TO THE PATIENT BASED ON THE COMPOSITE STIMULATION-EVOKED SIGNAL

FIG. 11A                    FIG. 11B                    FIG. 11C

Update Therapy Based on Signal + Sensory Information

NEUROSTIMULATION RESPONSE AND CONTROL

RELATED APPLICATIONS

This application claims the benefit of U.S. Provisional Application Ser. No. 63/175,394 (filed Apr. 15, 2021) and 63/246,592 (filed Sep. 21, 2021), each entitled "NEURO-STIMULATION RESPONSE AND CONTROL" and are incorporated by reference herein in their entireties.

TECHNICAL FIELD

This disclosure generally relates to medical devices, and more specifically, electrical stimulation.

BACKGROUND

Electrical stimulation devices, sometimes referred to as neurostimulators or neurostimulation devices, may be external to or implanted within a patient, and configured to deliver electrical stimulation therapy to various tissue sites to treat a variety of symptoms or conditions such as retention, overactive bladder, urgency, urgency frequency, urinary incontinence, bladder incontinence, fecal incontinence, sexual dysfunction, obesity, gastroparesis, intractable constipation, pelvic pain, chronic pain, irritable bowel syndrome, inflammatory bowel disease, interstitial cystitis, neurogenic bowel/bladder (neurological disorders: tremor, Parkinson's disease, epilepsy, multiple sclerosis, stroke, spinal cord injury, neuropathy etc.). An electrical stimulation device may deliver electrical stimulation therapy via electrodes, e.g., carried by one or more leads, positioned proximate to target locations associated with the brain, the spinal cord, nerves of the pelvis and pelvic floor, tibial nerves, peripheral nerves, the gastrointestinal tract, or elsewhere within a patient. Stimulation proximate the spinal cord, proximate the sacral nerves, within the brain, and proximate peripheral nerves is often referred to as spinal cord stimulation (SCS), sacral neuromodulation (SNM), deep brain stimulation (DBS), and peripheral nerve stimulation (PNS), respectively.

A physician, clinician, or patient may select values for a number of programmable stimulation parameters in order to define the electrical stimulation therapy to be delivered by the implantable stimulator to a patient. For example, the physician or clinician may select one or more electrodes, polarities of selected electrodes, a voltage or current amplitude, a pulse width, a pulse frequency, a cycling, and a duration of stimulation as stimulation parameters. A set of therapy stimulation parameters, such as a set including electrode combination or configuration, electrode polarity, amplitude, pulse width, pulse shape, pulse frequency or pulse rate, or cycling may be referred to as a therapy program in the sense that they define the electrical stimulation therapy to be delivered to the patient.

SUMMARY

In one example, this disclosure describes a method that includes delivering one or more electrical stimulation signals to a patient; sensing a composite stimulation-evoked signal comprising a composite of signals generated by one or more signal sources in response to the one or more electrical stimulation signals; and controlling delivery of electrical stimulation therapy to the patient based on the composite stimulation-evoked signal.

In another example, this disclosure describes a system that includes at least one electrode configured to deliver the electrical stimulation to a patient; and a device that includes processing circuitry configured to: deliver one or more electrical stimulation signals to the patient; sense a composite stimulation-evoked signal comprising a composite of electrical signals generated by one or more signal sources in response to the one or more electrical stimulation signals; and control delivery of electrical stimulation therapy to the patient based on the composite stimulation-evoked signal.

In another example, this disclosure describes a computer readable medium that includes instructions that when executed cause one or more processors to: deliver one or more electrical stimulation signals to a patient; sense a composite stimulation-evoked signal comprising a composite of signals generated by one or more signal sources in response to the one or more electrical stimulation signals; and control delivery of electrical stimulation therapy to the patient based on the composite stimulation-evoked signal.

In any of the above examples, the composite of signals may be signals from one or more signal sources in response to the electrical stimulation. For instance, two or more signals may come from one signal source or more than one signal source.

The details of one or more examples are set forth in the accompanying drawings and the description below. Other features, objects, and advantages will be apparent from the description, drawings, and claims. The summary is intended to provide an overview of the subject matter described in this disclosure. It is not intended to provide an exclusive or exhaustive explanation of the systems, device, and methods described in detail within the accompanying drawings and description below. Further details of one or more examples of this disclosure are set forth in the accompanying drawings and in the description below. Other features, objects, and advantages will be apparent from the description and drawings, and from the claims.

DETAILED DESCRIPTION

Figure 1:
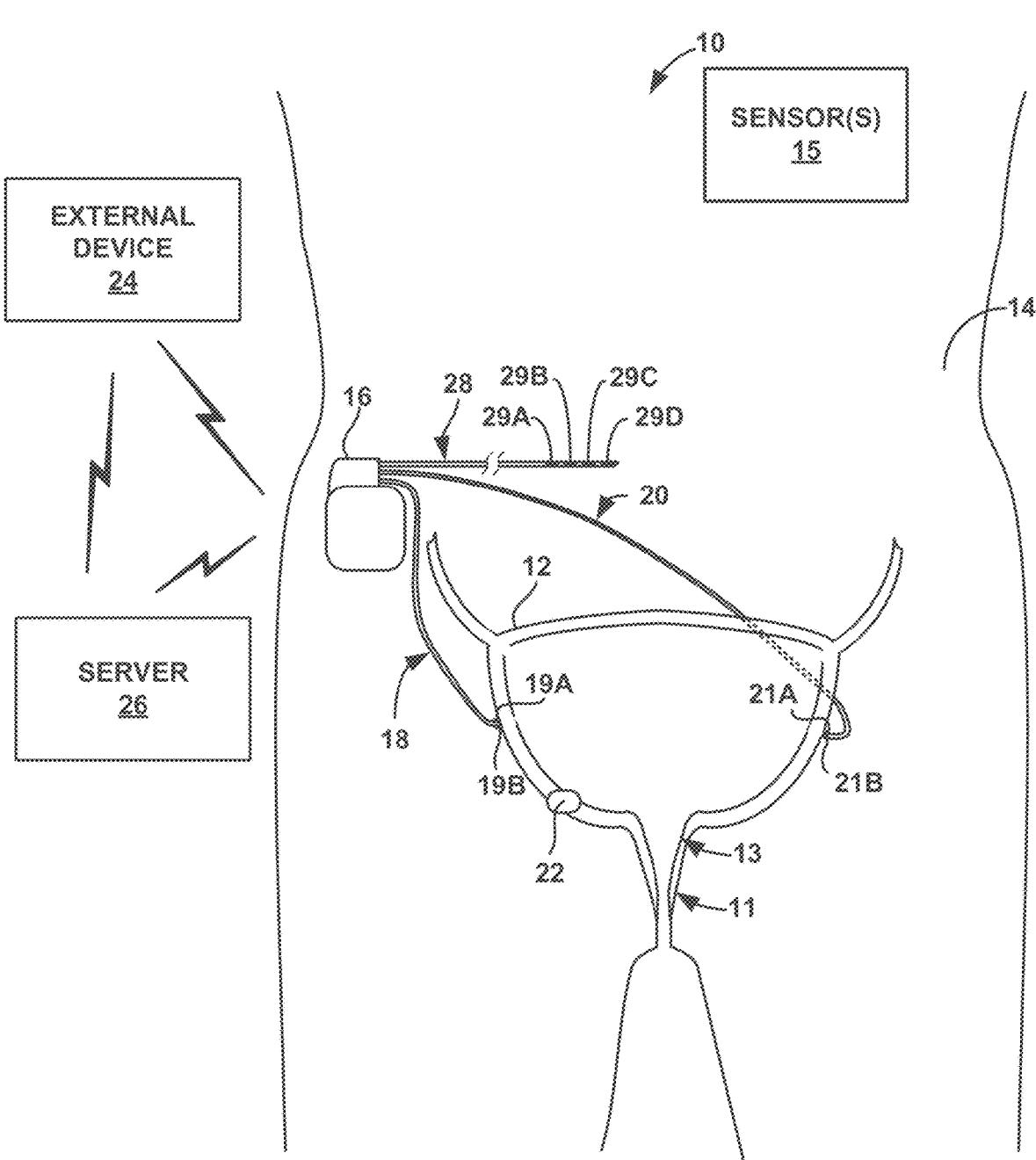
FIG. 1 is a conceptual diagram illustrating an example system that includes an implantable medical device (IMD) in the form of a neurostimulation device configured to deliver sacral neuromodulation (SNM), an external programmer, and one or more sensing devices in accordance with one or more techniques of this disclosure.

Electrical stimulation therapy, e.g., sacral nerve stimulation, tibial nerve stimulation, and/or other types of invasive or noninvasive neuromodulation, may provide bladder and/or bowel dysfunction therapy, pain relief and/or other therapeutic benefits. For example, stimulation therapy to address bladder and/or bowel dysfunction including, but not limited to, retention, overactive bladder, urgency, urgency frequency, urinary incontinence, bladder incontinence, fecal incontinence, sexual dysfunction, obesity, gastroparesis, intractable constipation, pelvic pain, chronic pain, irritable bowel syndrome, inflammatory bowel disease, interstitial cystitis, neurogenic bowel/bladder (e.g. caused by neurological disorders: tremor, Parkinson's disease, epilepsy, multiple sclerosis, stroke, spinal cord injury, neuropathy etc.

Electrical stimulation may evoke a response (e.g., a signal) such as a neural response of one or more nerves, electrical activity of muscles, and contractions of one or more muscles. For example, stimulation of sacral nerves through electrical leads implanted near sacral nerves via sacral neuromodulation may evoke a neural response in adjacent nerves, muscle contractions within the pelvic floor, and distal contractions in the foot. The neural response in nerves and activation/contraction of muscles evoked by electrical stimulation may be captured (e.g., or detected, sensed, measured, and the like) as a stimulation-evoked signal that may be a composite signal generated from signals from one or more signal sources.

A stimulation-evoked signal may include one or more features that may indicate one or more aspects of electrical stimulation therapy delivery, such as a positioning of electrical lead(s) that provides effective therapy, e.g., electrical lead placement that improves symptoms and/or disease systems. Stimulation-evoked signals, changes in stimulation-evoked signals, or a lack thereof, e.g., a lack of activation/response/contraction in response to electrical stimulation, may indicate a placement of the electrical lead that does not provide effective therapy, e.g., poor electrical lead placement and subsequent therapy. Capturing and processing stimulation-evoked signals in an operating room, a clinic, at home, or in other environments presents several challenges. Those challenges may be due to the limitations of the device (configuration, firmware, hardware), difficulty in receiving the signal due to noise (i.e. biological noise), subjectivity and difficulty in processing/interpretation; ability to understand clinical significance on the signal to support decision making.

The present disclosure addresses those difficulties by providing a robust manner to capture signals received in response to delivery of electrical stimulation by detecting a composite signal of multiple signals evoked by multiple signal sources (e.g., nerves and/or muscles) in response to delivery of electrical stimulation therapy. By detecting a composite signal comprised of multiple signals from one or more sources, the detected composite signal can be used to more accurately or more reliably assess, for example but not limited to, efficacy of response to stimulation, determine or adjust stimulation settings (e.g. stimulation parameters, timing, lead activation); determine or adjust stimulation therapy (e.g., timing and duration of stimulation), lead placement and efficacy (e.g. positioning or repositioning during trial stimulation (external/implant) or chronic implantation).

Stimulation systems and embodiments described herein may utilize chronic neurostimulators or trial neurostimulators. Chronic neurostimulators are usually implanted and are intended to provide long term therapy (e.g. 5-20 years). For sacral neuromodulation, chronic implants typically include a battery that is connected to a lead with electrodes. Trial neurostimulators are temporary neurostimulators to determine if the patient will be responsive to treatment. Trial neurostimulators are usually an external battery/stimulator that couples to an implanted lead (e.g. a temporary lead), but may also be implanted or partially implanted.

In accordance with one or more techniques of this disclosure, example electrical stimulation systems and example techniques may utilize stimulation-evoked signals for determining one or more aspects of electrical stimulation therapy delivery, such as lead positioning, stimulation parameters, stimulation timing, and the like. For example, a medical device may output one or more electrical stimulation signals (e.g., waveforms) via stimulation electrodes on a lead, and sensing electrodes on the same lead or a different lead may sense one or more neural responses and/or one or more muscle activation/contraction responses as one or more stimulation-evoked signals. One or more electrodes that provide the stimulation may be the same as one or more sensing electrodes or different. In some examples, one or more sensing electrodes may sense a composite stimulation-evoked signal that is a composite of signals generated by one or more signal sources, e.g., nerves and/or muscles, in response to the delivered electrical stimulation signals. For example, the sensed composite stimulation-evoked signal may be a composite of signals from one or more nerves, one or more muscles, or at least one muscle and at least one nerve captured concurrently within a particular amount of time. In some examples, the signals generated by two more signal sources may be stimulation-evoked signals. For example, the sensed composite stimulation-evoked signal may be a composite of signals from two or more nerves, two or more muscles, or at least one muscle and at least one nerve captured concurrently within a particular amount of time. The particular amount of time may be an amount of time starting when the electrical stimulation begins or ends, and ending after a predetermined amount of time has passed, or ending based on the composite stimulation-evoked signal, one or more of the constituent signals of the composite stimulation-evoked signal, or some other trigger such as a physiological response or patient-input response is received, or ending based on other criteria. In some examples, a composite stimulation-evoked signal may be a composite of two or more signals generated by single signal source, e.g., at different times and captured within a particular amount of time. For example, delivery of an electrical stimulation signal may cause multiple responses from a single signal source, e.g., a muscle or nerve, and each response of the signal source may generate a signal (e.g., a stimulation-evoked signal).

In some examples, a composite stimulation-evoked signal may include signal features indicative of the responses of one or more signal sources (e.g., nerves or muscles) that occur over a period of time. The capture period for composite signals may change based on location, stimulation amplitude and electrode configuration. In some instances, the composite stimulation-evoked signal is captured over a time period that is e.g., more than 5 milliseconds (ms), more than 10 ms, more than 20 ms, etc. Or less than 100 ms, less than 80 ms, less than 60 ms, etc. For example, EMGs may be detected over time periods between 0 ms-30 ms. In other words, a composite stimulation-evoked signal may contain information relating to the efficacy of electrical stimulation therapy from the responses of the signal source(s) and may occur over a period of time (e.g., a signal capture time window). For example, a time window may be chosen to account for different signal sources having different response times, e.g., neural responses versus muscle contractions/responses, and the different sources may be located at different distances from both the electrical stimulation source (e.g., an electrode of a lead) and a sensor (e.g., which may be the same and/or a different electrode on the same and/or different lead, or a different sensor located within and/or external to the patient's body). In order to capture at least a portion or substantially all of each of the stimulation-evoked signals from the different signal sources, the signal capture time window may be longer than any single stimulation-evoked signal because of the varying response times, temporal signal lengths, and signal source distances. For example, a time window may be selected to capture a composite signal of one ore neural signals received within, e.g., 2 ms or 3 ms of the stimulation pulse, one or more muscle contraction signals received within 15 ms of the stimulation pulse, and one or more muscle reflex signals received within 75 ms. In some examples, the timing of the sensing or detection of stimulation-evoked signals may depend on how fast a particular signal source activates, e.g., adjacent nerves may be the fastest (e.g., shortest response time) and a muscle and any post-synaptic neural activation may be slower (e.g., have a longer response time). The timing of the sensing/receipt of stimulation-evoked signals may also depend on how close the signal source is to the sensing/capturing electrode, e.g., for the transmission time for the signal to get to the electrode.

In some examples, a composite stimulation-evoked signal may comprise one or more compound action potentials, e.g., an evoked compound action potential (ECAP). In some examples, the composite stimulation-evoked signal may comprise more than a compound action potential, e.g., one or more of an ECAP, an EMG or surface EMG, mechano-myography (e.g., an MMG), a network excitability, and/or multiple signals of differing signal type evoked by one or more signal sources. In some examples, signal sources may include nerves such as sacral nerves, dorsal and ventral rami of sacral nerves, pudendal nerves, sciatic nerves, saphenous nerves, nerves in the sacral plexus, pelvic nerves, pelvic plexus nerves, pelvic splanchnic nerves, inferior hypogastric plexus nerves, lumbosacral trunk nerves, e.g., where the lumbosacral trunk joins sacral nerves, any sympathetic nerve fibers in the sympathetic chain of any of the above nerves or other nerves. In some examples, signal sources may include muscles such as an external anal sphincter muscle, rectum, coccygeus muscle, levator ani muscle group, bulbocavernosus and/or bulbospongiosus muscle, gluteal muscles, e.g., gluteal maximus, gluteal medius, and gluteal minimus, perineal muscles, ischiocavernosus muscles, puborectalis muscles, piriformis muscles, or any other muscles.

In some examples, the composite stimulation-evoked signal may be a combination of any and/or all of the various signal sources. For example, an electrical stimulation signal may cause a nerve and/or muscle proximate to the stimulation signal to generate a response and other nerves or muscles, not necessarily proximate to the stimulation signal, may also generate responses. In some examples, an electrical stimulation signal may cause a proximate nerve to respond and/or directly activate one or muscles and causing those one or more muscles to response. In some examples, the electrical stimulation signal may be applied to, or proximate to, the spinal cord which may respond with a reflex and/or reflex signal, e.g., one or more nerve fibers may evoke one or more reflexes and/or reflex signals, which may be stimulation-evoked signals. Additionally, muscle reflexes that results in a signal may be elicited from proximate nerves via the spinal cord. The composite stimulation-evoked signal may be a composite of signals from any of the multiple signal sources.

In some examples, the system may be configured to determine features based on the captured composite signal, and therapy efficacy may be determined based on the features and/or a collection of features captured from a collection of patients. For example, machine learning may be used on a collection of features from patient composite signals and paired with stimulation outcome measures to build a classification algorithm that can predict patient therapy response outcome and therapy efficacy. In some examples, the predicted therapy efficacy may then be used to make therapy decisions, e.g., implant left or right side, choose the optimal foramen, implant leads or not implant leads, choose an electrode configuration, tune stimulation parameters, and the like. A primary example includes positioning or repositioning the lead for target therapeutic response.

In certain embodiments, the system may be configured to identify the dynamic response of the composite signals as features for determining therapy efficacy. Such features of the composite signal may include, for example, changes in response to changing stimulation patterns (e.g. amplitude, pulse width; frequency); changes to composite signal in response to transmitted signal at different periods of time (nighttime v. daytime); changes in composite signal in response to transmitted signal based on movement or patient positioning; changes in composite signal in response to state of bladder or bowel (e.g. empty/full).

The various features of the composite signal described herein may be used to guide therapy or predict efficacy. Features of the composite signal may be used to determine the optimal side for implantation. For example, a test implant may be used to evoke and measure composite signals to guide subsequent implantation of the primary device. During the testing phase, signals from different placed sensors may be recorded separately or independently, and features of the composite signal (e.g. strength of response, no response, low response, high response) at the sensors can be used to guide implant placement. In some embodiments, features of the composite signal may include differences in response compared to historical data or difference in response to stimulation polarity (e.g. monopolar or bipolar). Features of the composite signal may also be used to predict or assess improvement for responders. For example, certain composite signals or strength of signals may indicate a likelihood of success, which may predict improvement as a sliding scale response or percentage. Features of the composite signal may be used to predict or assess durability. Durability may be indicated by the ability for a patient's neurostimulation therapy to maintain an improvement of symptoms and, e.g., tracking the composite signals in response to the maintenance period for trending. Durability may be indicated by the consistency of composite signals over time. For example, certain composite signals or strength of signals may indicate whether the therapy is likely to fade over time. Features of the composite signal may also be used to determine optimal therapy based on the response. For example, features of the composite signal may be measured in response to various stimulation patterns, and depending on the response, an ideal stimulation pattern may be indicated.

Systems and methods of the invention may involve composite signals obtained from one or more different sources. In some instances, the system may selectively identify particular signals in the composite signal based on certain features. For example, whether a signal source or multiple sources are used may be based on the following one or more of the features: stimulation pattern, time of day, movement/positional changes, status of the composite signal (variable or plateauing) and state of the bladder or bowel.

To maintain signal stability of a composite signal, the stimulation pattern may be adjusted to maintain the physiological response. For example, positive results may be shown from a composite signal having a certain amplitude, the system may automatically adjust stimulation signal to maintain a composite signal that relates to the positive results. This automatic maintenance may be time limited or keyed to one or more of following features: stimulation pattern, time of day, movement/positional changes, status of the composite signal (variable or plateauing) and status of state of the bladder/bowel. In another example, the system may determine a representative composite signal, and define those signal features as a target, such that stimulation parameters are automatically or manually adjusted to achieve and maintain the evoked signal in a range comparable to the target Systems and methods for sensing a composite stimulation-evoked signal are described herein. The system may include a stimulator system that interacts with a stimulator programmer. Various examples are discussed relative to one or more stimulation devices. It is recognized that the stimulation devices may include features and functionality in addition to electrical stimulation. Many of these additional features are expressly discussed herein. A few example features include, but are not limited to, different types of sensing capabilities and different types of wireless communication capabilities. For ease of discussion, the present disclosure does not expressly recite every conceivable combination of the additional features, such as by repeating every feature each time different examples and uses of the stimulation devices are discussed.

FIG. 1 is a conceptual diagram illustrating an example system 10 that includes an implantable medical device (IMD 16) in the form of a neurostimulation device configured to deliver sacral neuromodulation (SNM), an external programmer, and one or more sensing devices in accordance with one or more techniques of this disclosure. While FIG.

1 illustrates an implantable medical device, it is understood that concepts disclosed herein may apply to external or trial neurostimulators. In some examples, system 10 may determine one or more stimulation setting(s) and manage delivery of neurostimulation to patient 14, e.g., to address bladder and/or bowel dysfunction including, but not limited to, retention, overactive bladder, urgency, urgency frequency, urinary incontinence, bladder incontinence, fecal incontinence, sexual dysfunction, obesity, gastroparesis, intractable constipation, pelvic pain, chronic pain, irritable bowel syndrome, inflammatory bowel disease, interstitial cystitis, neurogenic bowel/bladder (e.g. caused by neurological disorders: tremor, Parkinson's disease, epilepsy, multiple sclerosis, stroke, spinal cord injury, neuropathy etc. As shown in the example of FIG. 1, therapy system 10 includes an implantable medical device (IMD) 16 (e.g., an example medical device), which may be coupled to one or more leads 18, 20, and 28 and/or one or more sensor 22. System 10 also includes an external device 24, which is configured to communicate with IMD 16 via wireless communication. For example, IMD may be connected to one or more lead 28 with one or more electrodes 29A-D. System 10 also includes server 26 which may be one or more servers in a cloud computing environment. Server 26 may be configured to communicate with external device 24 and/or IMD 16 via wireless communication through a network access point (not shown in FIG. 1) and may be collocated with external device 24 or may be located elsewhere, such as in a cloud computing data center. IMD 16 generally operates as a therapy device that delivers neurostimulation (e.g., electrical stimulation in the example of FIG. 1) to, for example, a target tissue site proximate a spinal nerve, a sacral nerve, a pudendal nerve, dorsal genital nerve, a tibial nerve, a saphenous nerve, an inferior rectal nerve, a perineal nerve, or other pelvic nerves, branches of any of the aforementioned nerves, roots of any of the aforementioned nerves, ganglia of any of the aforementioned nerves, or plexus of any of the aforementioned nerves. IMD 16 provides electrical stimulation to patient 14 by generating and delivering a programmable electrical stimulation signal (e.g., in the form of electrical pulses or an electrical signal) to a target a therapy site near lead 28 and, more particularly, near electrodes 29A-29D (collectively referred to as "electrodes 29") disposed proximate to a distal end of lead 28.

IMD 16 may be surgically implanted in patient 14 at any suitable location within patient 14, such as near the pelvis. In some examples, IMD 16 may be implanted in a subcutaneous location in the side of the lower abdomen or the side of the lower back or upper buttocks. IMD 16 has a biocompatible housing, which may be formed from titanium, stainless steel, a liquid crystal polymer, or the like. The proximal ends of leads 18, 20, and 28 are both electrically and mechanically coupled to IMD 16 either directly or indirectly, e.g., via respective lead extensions. Electrical conductors disposed within the lead bodies of leads 18, 20, and 28 electrically connect to sense electrodes (e.g., electrodes 19A, 19B, 21A, 21B, 29A, 29B, 29C, and 29D) and stimulation electrodes, such as electrodes 19A, 19B, 21A, 21B, 29A, 29B, 29C, and 29D, to sensing circuitry and a stimulation delivery circuitry (e.g., a stimulation generator) within IMD 16. In the example of FIG. 1, leads 18 and 20 carry electrodes 19A, 19B (collective referred to as "electrodes 19") and electrodes 21A, 21B (collectively referred to as "electrodes 21"), respectively. As described in further detail below, electrodes 19 and 21 may be positioned for sensing an impedance of bladder 12, which may increase as the volume of urine within bladder 12 increases. In some examples, system 10 may include electrodes (such as electrodes 19 and 21), a strain gauge, one or more accelerometers, ultrasound sensors, optical sensors, or any other sensor. In some examples, the sensors may be configured to gather information relating to the patient, such as detect contractions of bladder 12, pressure or volume of bladder 12, or any other indication of the fill cycle of bladder 12 and/or possible bladder dysfunctional states. In some examples, system 10 may use sensors other than electrodes 19 and 21 for sensing information relating to the patient, such as bladder volume. System 10 may use the sensor data for determining stimulation program settings for a given patient, as discussed below. IMD 16 may communicate sensed data to server 26. In some examples, IMD 16 may communicate the sensor data through external device 24. In other examples, IMD 16 may communicate the sensor data to server 26 without communicating the sensor data through external device 24.

In some examples, external device 24 may collect user input identifying a voiding event, perceived level of fullness, or any other indication of an event associated with the patient. The user input may be in the form of a voiding journal analyzed by external device 24, IMD 16 or server 26, or individual user inputs associated with respective voiding events, leakage, or any other event related to the patient. External device 24 may provide this user input to server 26.

One or more medical leads, e.g., leads 18, 20, and 28, may be connected to IMD 16 and surgically or percutaneously tunneled to place one or more electrodes carried by a distal end of the respective lead at a desired nerve or muscle site, e.g., one of the previously listed target therapy sites such as a tissue site proximate a spinal (e.g., sacral) or pudendal nerve. For example, lead 28 may be positioned such that electrodes 29 deliver electrical stimulation to a spinal, sacral or pudendal nerve to reduce a frequency and/or magnitude of contractions of bladder 12. Additional electrodes of lead 28 and/or electrodes of another lead may provide additional stimulation therapy to other nerves or tissues as well. In FIG. 1, leads 18 and 20 are placed proximate to an exterior surface of the wall of bladder 12 at first and second locations, respectively. In other examples of therapy system 10, IMD 16 may be coupled to more than one lead that includes electrodes for delivery of electrical stimulation to different stimulation sites within patient 14, e.g., to target different nerves.

In the example shown in FIG. 1, leads 18, 20, 28 are cylindrical. Electrodes 19, 21, 29 of leads 18, 20, 28, respectively, may be ring electrodes, segmented electrodes, partial ring electrodes or any suitable electrode configuration. Segmented and partial ring electrodes each extend along an arc less than 360 degrees (e.g., 90-120 degrees) around the outer perimeter of the respective lead 18, 20, 28. In some examples, segmented electrodes 29 of lead 28 may be useful for targeting different fibers of the same or different nerves to generate different physiological effects (e.g., therapeutic effects). In examples, one or more of leads 18, 20, 28 may be, at least in part, paddle-shaped (e.g., a "paddle" lead), and may include an array of electrodes on a common surface, which may or may not be substantially flat. Additionally, in the case of trial stimulation, the lead may be a peripheral nerve evaluation (PNE) lead to provide temporary neural stimulation. The PNE lead may include one or more leads, with typical trial leads including one electrode with an external ground.

In some examples, one or more of electrodes 19, 21, 29 may be cuff electrodes that are configured to extend at least partially around a nerve (e.g., extend axially around an outer surface of a nerve). Delivering electrical stimulation via one or more cuff electrodes and/or segmented electrodes may help achieve a more uniform electrical field or activation field distribution relative to the nerve, which may help minimize discomfort to patient 14 that results from the delivery of electrical stimulation. An electrical field may define the volume of tissue that is affected when the electrodes 19, 21, 29 are activated. An activation field represents the neurons and/or muscles that will be activated by the electrical field in the neural tissue proximate to the activated electrodes.

The illustrated numbers and configurations of leads 18, 20, and 28 and electrodes carried by leads 18, 20, and 28 are merely exemplary. Other configurations, e.g., numbers and positions of leads and electrodes are also contemplated. For example, in other implementations, IMD 16 may be coupled to additional leads or lead segments having one or more electrodes positioned at different locations proximate the spinal cord or in the pelvic region of patient 14. The additional leads may be used for delivering different stimulation therapies or other electrical stimulations to respective stimulation sites within patient 14 or for monitoring at least one physiological marker of patient 14.

In accordance with some examples of the disclosure, IMD 16 delivers electrical stimulation to at least one of a spinal nerve (e.g., a sacral nerve), a pudendal nerve, dorsal genital nerve, a tibial nerve, a saphenous nerve, an inferior rectal nerve, or a perineal nerve to provide a therapeutic effect that reduces or eliminates a dysfunctional state such as overactive bladder. The desired therapeutic effect may be an inhibitory physiological response related to voiding of patient 14, such as a reduction in bladder contraction frequency by a desired level or degree (e.g., percentage), a reduction in bladder afferent firing, altering a pelvic floor muscle/nerve response and/or status such as of the external urethral sphincter (EUS), levator ani nerve, external anal sphincter, and the like.

A stimulation program may define various parameters of the stimulation signal and electrode configuration which result in a predetermined stimulation intensity being delivered to the targeted nerve or tissue. In some examples, the stimulation program defines parameters for at least one of a current or voltage amplitude of the stimulation signal, a frequency or pulse rate of the stimulation, the shape of the stimulation signal, a duty cycle of the stimulation, a pulse width of the stimulation, a duty cycle of the stimulation ON/OFF periods, and/or the combination of electrodes 29 and respective polarities of the subset of electrodes 29 used to deliver the stimulation. Together, these stimulation parameter values may be used to define the stimulation intensity (also referred to herein as a stimulation intensity level). In some examples, if stimulation pulses are delivered in bursts, a burst duty cycle also may contribute to stimulation intensity. Also, independent of intensity, a particular pulse width and/or pulse rate may be selected from a range suitable for causing the desired therapeutic effect. In addition, as described herein, a period during which stimulation is delivered may include on and off periods (e.g., a duty cycle or bursts of pulses) where even the short inter-pulse durations of time when pulses are not delivered are still considered part of the delivery of stimulation. A period during which system 10 withholds stimulation delivery is a period in which no stimulation program is active for IMD 16 (e.g., IMD 16 is not tracking pulse durations or inter-pulse durations that occur as part of the electrical stimulation delivery scheme). In addition to the above stimulation parameters, the stimulation may be defined by other characteristics, such as a time for which stimulation is delivered, a time for which stimulation is terminated, and times during which stimulation is withheld.

In certain embodiments, stimulation will be provided below or at sensory threshold of the patient, but sometimes, in order to evoke or maintain a certain physiological response (i.e. composite signal), the stimulation may be provided above the sensory threshold.

System 10 may also include an external device 24, as shown in FIG. 1. External device 24 may be an example of a computing device. In some examples, external device 24 may be a clinician programmer or patient programmer, such as patient programmer 300 described below. In some examples, external device 24 may be a device for inputting information relating to a patient. In some examples, external device 24 may be a wearable communication device, with a therapy request input integrated into a key fob or a wrist-watch, handheld computing device, smart phone, computer workstation, or networked computing device. External device 24 may include a user interface that is configured to receive input from a user (e.g., patient 14, a patient caretaker or a clinician). In some examples, the user interface includes, for example, a keypad and a display, which may for example, be a liquid crystal display (LCD) or light emitting diode (LED) display. In some examples, the user interface may include a turnable knob or a representation of a turnable knob. The keypad may take the form of an alphanumeric keypad or a reduced set of keys associated with particular functions. External device 24 may addition-ally or alternatively include a peripheral pointing device, such as a mouse, via which a user may interact with the user interface. In some examples, a display of external device 24 may include a touch screen display, and a user may interact with external device 24 via the display. It should be noted that the user may also interact with external device 24, server 26 and/or IMD 16 remotely via a networked com-puting device.

A user, such as a patient, physician, technician, surgeon, electrophysiologist, or other clinician, may also interact with external device 24 or another separate programmer (not shown), such as a clinician programmer, to communicate with IMD 16 and/or server 26. Such a user may interact with external device 24 to retrieve physiological or diagnostic information from IMD 16. The user may also interact with external device 24 to program IMD 16, e.g., select values for the stimulation parameter values with which IMD 16 gen-erates and delivers stimulation and/or the other operational parameters of IMD 16, such as magnitudes of stimulation energy, user requested periods for stimulation or periods to prevent stimulation, or any other such user customization of therapy. In some examples, the stimulation parameter values may be proposed by system 10, for example, by server 26 and a user may be able to accept or reject the stimulation parameter values. In other examples, the stimulation param-eter values may be set by system 10, for example, by server 26. As discussed herein, the user may also provide input to external device 24 indicative of physiological events such as bladder fill level perception and void events.

In some examples, a user may utilize sensor 15, such as wearable sensors or existing implanted sensors, to collect patient data related to sleep, activity or disease symptoms. Sensor 15 may include one or more sensors, e.g., sensor(s) 15. For example, sensors 15 may be a heartrate sensor, an accelerometer and/or other sensor to collect patient data, for example, on disease symptoms or lifestyle. The patient data captured by the sensors, such as sensor 15, may be provided to server 26. In some examples, the sensors, such as sensor 15, may be configured to communicate with an external device, such as external device 24, via a wireless link. In some examples, external device 24 may collect the patient data generated by the sensors and send the patient data to server 26. In other examples, another device may collect the patient data generated by the sensors and send the patient data to server 26.

In some examples, IMD 16 and/or external device 24 may receive information from sensor 15 directly, e.g., via wire-less communication, or indirectly, such as from server 26 via a network connection. Sensor 15 may be positioned to sense one or more physiological responses at a selected location on patient 14. In some examples, sensor 15 may be posi-tioned at, attached to or near tissue for a target anatomical area, e.g., at a limb or appendage, such as at or on a leg, toe, foot, arm, finger or hand of patient 14, e.g., to sense an EMG, a galvanic skin response adjacent to placement of sensor 15, or other response. In some examples, sensor 15 may be attached to an appendage of the patient 14 to sense a physiological response associated with the appendage, e.g., by a clip-on mechanism, strap, elastic band and/or adhesive. In some examples, sensor 15 (or one of a plurality of sensors 15) may be implantable within patient 14, e.g., within a limb or appendage of the patient, near the spinal cord of the patient, within the brain of the patient, and the like.

In some examples, sensor 15 may be a physiological and/or patient posture or behavior sensor. For example, sensor 15 may be a heart rate monitor configured to detect and/or determine a heart rate and/or a heart rate variability. Sensor 15 may be configured to detect and/or determine a biopotential. Sensor 15 may be a thermometer configured to detect and/or determine a temperature of at least a part of the patient's anatomy. Sensor 15 may be configured to measure a pressure, e.g., a patient blood pressure, or to measure an impedance of at least a portion of the patient's anatomy. Sensor 15 may be a blood flow sensor that measures blood flow and provides information related to blood flow asso-ciated with tissue of the patient. For example, sensor 15 may provide blood flow values, or other information indicative of blood flow values or changes in blood flow values. The blood flow value may be an instantaneous blood flow measurement or may be a measurement of blood flow over a period of time such as average blood flow value, maximum blood flow value, minimum blood flow value during the period of time. In some examples, sensor 15 may be a microphone configured to detect/determine sounds of at least a portion of the patient's anatomy. In some examples, sensor 15 may comprise and accelerometer configured to detect and/or determine a position and/or patient movement, a patient movement history over a predetermined amount of time, and the like. In some examples, sensor 15 may be configured to receive patient 14 input such as a pain response, a pain score, an area of pain, an amount of paresthesia, an area of paresthesia, information relating to voiding and/or a voiding rate (e.g., voids per day), and the like. In some examples, sensor 15 may be an environmental sensor, such as a microphone, thermometer, hygrometer, pressure sensor, and the like, configured to detect and/or determine sounds, temperatures, humidity and pressure, etc., of the environment in which the patient 14 is located.

In some examples, the user may use external device 24 to retrieve information from IMD 16 relating to the contraction frequency of bladder 12 and/or voiding events. As another example, the user may use external device 24 to retrieve information from IMD 16 relating to the performance or integrity of IMD 16 or other components of system 10, such as leads 18, 20, and 28, or a power source of IMD 16. In some examples, this information may be presented to the user as an alert if a system condition that may affect the efficacy of therapy is detected.

The user of external device 24 may also communicate with server 26. For example, the user of external device 24 may provide information relating to the patient to server 26, such as demographic information, medical history, lifestyle information, bladder events, level satisfaction with therapy or sensor data.

Patient 14 may, for example, use a keypad or touch screen of external device 24 to request IMD 16 to deliver or terminate the electrical stimulation, such as when patient 14 senses that a leaking episode may be imminent or when an upcoming void may benefit from terminating therapy that promotes urine retention. In this way, patient 14 may use external device 24 to provide a therapy request to control the delivery of the electrical stimulation "on demand," e.g., when patient 14 deems the second stimulation therapy desirable. This request may be a therapy trigger event used to terminate electrical stimulation. Patient 14 may also use external device 24 to provide other information to IMD 16, such as information indicative of a phase of a physiological cycle, such as the occurrence of a voiding event.

External device 24 may provide a notification to patient 14 when the electrical stimulation is being delivered or notify patient 14 of the prospective termination of the electrical stimulation. In addition, notification of termination may be helpful so that patient 14 knows that a voiding event may be more probable and/or the end of the fill cycle is nearing such that the bladder should be emptied (e.g., the patient should visit a restroom). In such examples, external device 24 may display a visible message, emit an audible alert signal or provide a somatosensory alert (e.g., by causing a housing of external device 24 to vibrate). In other examples, the notification may indicate when therapy is available (e.g., a countdown in minutes, or indication that therapy is ready) during the physiological cycle. In this manner, external device 24 may wait for input from patient 14 prior to terminating the electrical stimulation that reduces bladder contraction or otherwise promotes urine retention. Patient 14 may enter input that either confirms termination of the electrical stimulation so that the therapy stops for voiding purposes, confirms that the system should maintain therapy delivery until patient 14 may void, and/or confirms that patient 14 is ready for another different stimulation therapy that promotes voiding during the voiding event.

In the event that no input is received within a particular range of time when a voiding event is predicted, external device 24 may wirelessly transmit a signal that indicates the absence of patient input to IMD 16. IMD 16 may then elect to continue stimulation until the patient input is received, or terminate stimulation, based on the programming of IMD 16. In some examples, the termination or continuation of electrical stimulation may be responsive to other physiological markers.

IMD 16 and external device 24 may communicate via wireless communication using any techniques known in the art. Examples of communication techniques may include, for example, low frequency or radiofrequency (RF) telemetry (such as Bluetooth), but other techniques are also contemplated. In some examples, external device 24 may include a programming lead that may be placed proximate to the patient's body near the IMD 16 implant site in order to improve the quality or security of communication between IMD 16 and external device 24.

IMD 16, in response to commands from external device 24, may deliver electrical stimulation therapy according to a one or more stimulation programs to a target tissue site of the patient 14 via any of electrodes 29A-29D, 19A-19B, and 21A-21B. In some examples, IMD 16 automatically modifies therapy stimulation programs as therapy needs of patient 14 evolve over time. For example, the modification of the therapy stimulation programs may cause the adjustment of at least one parameter of the plurality of stimulation pulses based on received information.

In the example four-wire arrangement shown in FIG. 1, electrodes 19A and 21A and electrodes 19B and 21B, may be located substantially opposite each other relative to the center of bladder 12. For example, electrodes 19A and 21A may be placed on opposing sides of bladder 12, either anterior and posterior or left and right. In FIG. 1, electrodes 19 and 21 are shown placed proximate to an exterior surface of the wall of bladder 12. In some examples, electrodes 19 and 21 may be sutured or otherwise affixed to the bladder wall. In other examples, electrodes 19 and 21 may be implanted within the bladder wall. To measure the impedance of bladder 12, IMD 16 may source an electrical signal, such as current, to electrode 19A via lead 18, while electrode 21A via lead 20 sinks the electrical signal. IMD 16 may then determine the voltage between electrode 19B and electrode 21B via leads 18 and 20, respectively. IMD 16 determines the impedance of bladder 12 using a known value of the electrical signal sourced the determined voltage.

In other examples, one or more electrodes 19, 21 29A-D may be used to detect an electromyogram (EMG) of the detrusor muscle. This EMG may be used to determine the frequency of bladder contractions and the physiological marker of patient 14. The EMG may also be used to detect the strength of the bladder contractions in some examples. As an alternative, or in addition, to an EMG, a strain gauge or other device may be used to detect the status of bladder 12, e.g., by sensing forces indicative of bladder contractions.

In the example of FIG. 1, IMD 16 also may include a sensor 22 for detecting changes in the contraction of bladder 12. Sensor 22 may include, for example, a pressure sensor for detecting changes in bladder pressure, electrodes for sensing pudendal or sacral nerve signals (e.g., afferent and/or efferent), electrodes for sensing urinary sphincter 11 or 13 EMG signals (or anal sphincter EMG signals in examples in which system 10 provides therapy to manage fecal urgency or fecal incontinence), or any combination thereof. In examples in which sensor 22 is a pressure sensor, the pressure sensor may be a remote sensor that wirelessly transmits signals to IMD 16 or may be carried on one of leads 18, 20, or 28 or an additional lead coupled to IMD 16. In some examples, IMD 16 may determine whether a contraction frequency of bladder 12 has occurred based on a pressure signal generated by sensor 22. In some examples, IMD 16 may control the timing of the delivery of the electrical stimulation based on input received from sensor 22.

Sensor 22 may comprise a patient motion sensor that generates a signal indicative of patient activity level or posture state. In some examples, IMD 16 may terminate the delivery of the electrical stimulation to patient 14 upon detecting a patient activity level exceeding a particular threshold based on the signal from the motion sensor. In other examples, IMD 16 may use sensor 22 to identify posture states known to require the desired therapeutic effect. For example, patient 14 may be more prone to an involuntary voiding event when patient 14 is in an upright posture state compared to a lying down posture state. In any event, one or more electrodes 19. 21, 22 and electrodes 29A-D may be configured to detect voiding events and/or the magnitude of a fill level of bladder 12 during the fill cycle. In some examples, IMD 16 may include sensor 22 and/or a motion sensor, e.g., within the housing of IMD 16.

As discussed above, system 10 may monitor the fill cycle of bladder 12 by detecting subsequent voiding events over time. In some examples, system 10 may detect voiding events by receiving an indication of a user input (e.g., via external device 24) representative of an occurrence of a voiding event. In other words, external device 24 may receive input from the user identifying that a voiding event occurred, the beginning of a voiding event, and/or the end of the voiding event. In other examples, system 10 may automatically detect voiding events without receiving user input via external device 24. System 10 may instead detect voiding events by detecting at least one of a pressure of the bladder, a flow of urine from the bladder, a wetness of an article external of the patient, a volume of the bladder, an EMG signal, a nerve recording, a posture change, a physical location of the patient within a structure such as a house or care facility, or a toilet use event. Some sensors external to patient 14 may communicate with external device 24 and/or IMD 16 to provide this information indicative of likely voiding events. For example, wetness may be detected by a moisture sensor (e.g., electrical impedance or chemical sensor) embedded in an undergarment worn by the patient and transmitted to IMD 16 or external device 24. Similarly, a toilet may include a presence sensor that detects when a patient is using the toilet (e.g., an infrared sensor, thermal sensor, or pressure senor) and transmits a signal indicating the presence of the patient to IMD 16 or external device 24. In this manner, non-invasively obtained data may provide information indicative of voiding events without implanted sensors. The information indicative of voiding events may be provided to server 26 by external device 24 or IMD 16. System 10 of FIG. 1 may implement the techniques of this disclosure.

In accordance with one or more aspects of this disclosure, one or more electrodes 19, 21, and 29 and/or sensor(s) 15 may be configured to sense, and IMD 16 and/or external device 24 may be configured to capture, a composite stimulation-evoked signal comprising a composite of signals generated by two or more signal sources in response to the one or more electrical stimulation signals. In some examples, IMD 16 and/or external device 24 may be configured to control delivery of electrical stimulation signals and/or therapy based on the composite stimulation-evoked signal. For example, IMD 16 and/or external device 24 may be configured to cause one or more electrodes 19, 21, and 29 to deliver one or more electrical stimulation signals to patient 14. In some examples, IMD 16 and/or external device 24 may cause one or more electrodes 19, 21, and 29A-D to deliver one or more electrical stimulation signals having non-equal pulse amplitudes, non-equal pulse durations, non-equal polarity and/or non-equal pulse frequencies. In other examples, IMD 16 and/or external device 24 may deliver various sweeps of different simulations signals to, for example, one or more electrodes 29A-D, for example sweeping at one or more electrodes sequentially over a period of time. The sweep may include same or different pulse widths, same or different stimulation level, etc. The sensing of one or more electrodes may be in response to the sweeps.

In some examples, IMD 16 and/or external device may be configured to deliver one or more electrical stimulation signals to a sacral nerve (e.g., for SNM therapy), the brain (e.g., DBS therapy), a peripheral nerve (e.g., for PNS and/or PNFS), a saphenous nerve, a tibial nerve, a pudendal nerve, a sciatic nerve, or any other suitable nerve, muscle, and or tissue of patient 14.

In some examples, one or more signal sources, such as two or more nerves, two or more muscles, or at least one muscle and at least one nerve, may respond to the electrical stimulation, e.g., via a neural response, a muscle contraction and/or activation, or any other response. In some examples, the response of the two or more sources may be electrical, e.g., an ECAP, an EMG or surface EMG, and the like. In some examples, the response may be mechanical and converted to an electrical signal by a sensor or detector, e.g., by a piezoresistive sensor or other sensor configured to measure muscle contraction and mechanomyography (MMG) and the like. In some examples, nerves may include any of the sacral nerves, e.g., dorsal and ventral rami of sacral nerves, pudendal nerves, sciatic nerves, saphenous nerves, nerves in the sacral plexus, pelvic nerves, pelvic plexus nerves, pelvic splanchnic nerves, inferior hypogastric plexus nerves, lumbosacral trunk nerves, e.g., where the lumbosacral trunk joins sacral nerves, any sympathetic nerve fibers in the sympathetic chain of any of the above nerves or other nerves. In some examples, one or more muscles may include an external anal sphincter muscle, coccygeus muscle, levator ani muscle group, bulbocavernosus and/or bulbospongiosus muscle, gluteal muscles, e.g., gluteal maximus, gluteal medius, and gluteal minimus, perineal muscles, ischiocavernosus muscles, puborectalis muscles, piriformis muscles, or any other muscles.

In some examples, the composite stimulation-evoked signal sensed by one or more sensors and/or electrodes may be a combination of any and/or all of the various signal sources. For example, an electrical stimulation signal may cause a nerve and/or muscle proximate to the stimulation signal to generate a response and other nerves or muscles, not necessarily proximate to the stimulation signal, may also generate responses. The composite stimulation-evoked signal may be a composite of signals from any of the multiple signal sources.

One or more sensors and/or electrodes, such as sensors 15, sensor 22, and/or electrodes 19, 21, and 29, may receive and/or sense signals from the two or more signal sources. In some examples, the received signals may be a composite, e.g., sensors 15, sensor 22, and/or electrodes 19, 21, and 29, may receive and/or sense the signals from two or more signal sources concurrently over a period of time as a single composite stimulation-evoked signal. For example, two or more signals may "arrive" at the sensor (or sensors or electrodes) at the same time and may add together forming the composite signal that is sensed. For example, the two or more signals may be electric signals which may add incoherently, coherently, constructively, destructively, and the like, to form the electric signal that is sensed. In other examples, the two or more signals may be individually sensed and then added and/or combined to for the composite stimulation-evoked signal. For example, electrodes 29 may sense an electric field caused by neural activity of nerve and a sensor 15 may sense an EMG signal caused by a contraction of a muscle, both in response to delivered electrical stimulation. IMD 16 and/or external device 24 may receive each stimulation-evoked signal from two or more sources and then combine the signals to form the composite stimulation-evoked signal.

In some examples, one or more electrodes, such as electrodes 29, may receive and/or sense signals from the one or more signal sources. In other words, electrodes 29 may sense one or more stimulation-evoked signals, or composite stimulation-evoked signals, alone. In some examples, the received signals may be a composite, e.g., electrodes 29, may receive and/or sense the signals from two or more signal sources concurrently over a period of time as a single composite stimulation-evoked signal. For example, two or more signals may "arrive" at electrodes 29 at the same time and may add together forming the composite signal that is sensed. For example, the two or more signals may be electric signals which may add incoherently, coherently, constructively, destructively, and the like, to form the electric signal that is sensed. In other examples, the two or more signals may be individually sensed and then added and/or combined to for the composite stimulation-evoked signal. For example, electrodes 29 may sense an electric field caused by neural activity of nerve and may sense an EMG signal caused by a contraction of a muscle, both in response to delivered electrical stimulation. IMD 16 and/or external device 24 may receive each stimulation-evoked signal from each of the two or more sources and then combine the signals to form the composite stimulation-evoked signal.

In some examples, the two or more signal sources may be located relatively far from a sensor/electrode (e.g., sensors 15, sensor 22, and/or electrodes 19, 21, and 29) and/or each other, e.g., at least 5 millimeters (mm) from the sensor and/or electrode and/or each other, at least 10 mm from the sensor and/or electrode and/or each other, at least 100 mm from the sensor and/or electrode and/or each other, at least 200 mm from the sensor and/or electrode and/or each other, at least 1 meter from the sensor and/or electrode and/or each other. For example, two or more signal sources may include a tibial nerve responding to sacral nerve stimulation. Ideally for ECAP signals, the sensing electrode is positioned near the signal source, e.g. 20 mm or less.

In some examples, the composite stimulation-evoked signal may have a relative long duration, e.g., more than 5 milliseconds (ms), more than 10 ms, more than 20 ms, etc, as compared to relatively shorter durations, e.g. less than 5 ms, less than 3 ms, less than 1 ms. For example, because the composite stimulation-evoked signal may originate from multiple signal sources at multiple distances from one or more the sensors and/or electrodes, and because different signal sources may have different response times, the signals from the signal sources may arrive at, and be captured by, a sensor and/or electrode at different times. In some examples, a sensor and/or electrode may sense signals from signal sources after delivery of every electrical stimulation signal, or a sensor and/or electrode may sense signals from signal sources after an amount of time after delivery of electrical stimulation signals. In some examples, the composite stimulation-evoked signal may comprise signals of different types from different signal sources. For example, the composite stimulation-evoked signal may comprise an ECAP signal generated relatively quickly after delivery of electrical stimulation signals, e.g., within 10 ms, and an EMG signal generated relatively slowly after delivery of electrical stimulation signals, e.g., after 0.1 ms, 0.5 ms, 5 ms. In some examples, the composite stimulation-evoked signal may comprise signals from multiple signal sources that do not overlap in time. For example, the composite stimulation-evoked signal may comprise an ECAP signal from a signal source relative close to the sensor and/or electrode followed by an EMG signal or another ECAP signal from a different signal source that may be relatively far from the sensor and/or electrode, e.g., such that the ECAP from the close signal source is no longer present while the EMG signal and/or ECAP from the more distant signal source are received by the sensor and/or electrode.

In some examples, IMD 16 and/or external device 24 may be configured to determine one or more features of the sensed stimulation-evoked signals and/or composite signal. For example, IMD 16 and/or external device 24 may be configured to determine signal peaks, peak amplitudes, number of peaks, areas under peaks, peak widths, time between peaks, ratios of peak amplitudes, widths, and/or areas, peak latency, signal valleys, valley amplitudes, number of valleys, areas above valleys, valley widths, time between valleys, ratios of valley amplitudes, widths, and/or areas, valley latency, root-mean-square signal value, signal skew, kurtosis, frequency and/or spectral content of the signal(s), or any other suitable signal feature, including a ratio or other statistical analysis for the foregoing. In other examples, IMD 16 and/or external device may be able to determine the stability of signals over time or stability of signals in comparison to historical data. In further examples, IMD 16 and/or external device may be able to identify differences in signals induced by cathodic pulse v. anodic pulse, or monopolar v. bipolar stimulation. In some examples, IMD 16 and/or external device 24 may be configured to determine an amplitude of one or more peaks of a composite stimulation-evoked signal that are greater than 1 millivolt (mV), or greater than 0.1 mV, or greater than 0.01 mV, or greater than 0.001V. In addition, signal might be measured at multiple amplitudes, and the growth curve with one of the above features can be utilized to estimate rate of growth of the signal, or neural threshold, or inflection point.

In some examples, IMD 16 and/or external device 24 may be configured to determine one or more classifications of the one or more determined features. For examples, IMD 16 and/or external device 24 may be configured to execute a trained machine learning (ML) algorithm to determine and use the classifications and to predict therapy efficacy based on the determined classifications. In some examples, IMD 16 and/or external device 24 may be configured to output the stimulation-evoked signals and/or determined features to an external device for processing, e.g., an external device, such as server 26, may execute the ML algorithm and communicate results to IMD 16 and/or external device 24. In some examples, IMD 16 and/or external device 24 may be configured to control therapy delivery based on the classifications and/or ML output or predictions.

In some examples, IMD 16 and/or external device 24 may be configured to control one or more electrical stimulation parameters based on composite stimulation-evoked signal(s). For example, IMD 16 and/or external device 24 may be configured to control therapy parameters such as stimulation amplitude, frequency, pulse width, and cycling based on the sensed stimulation-evoked signal(s). In some examples, IMD 16 and/or external device 24 may be configured provide feedback to a user and/or clinician, e.g., via a display screen, and a user and/or clinician may adjust therapy parameters, lead placement and/or positioning, the timing of therapy delivery. In some example examples, IMD 16 and/or external device 24 may be configured to bypass changes to therapy, e.g., based on a determination that the therapy is effective, e.g., based on composite stimulation-evoked signal(s).

Although the example of FIG. 1 is directed to management of bladder dysfunction, in other examples, system 10 may be configured to treat other conditions that may benefit from neurostimulation therapy. For example, system 10 may be used to treat tremor, Parkinson's disease, epilepsy, or other neurological disorders, urinary or fecal incontinence, sexual dysfunction, obesity, or gastroparesis, or psychiatric disorders such as depression, mania, obsessive compulsive disorder, or anxiety disorders. Hence, in some examples, system 10 may be configured to deliver sacral neuromodulation (SNM), sacral neurostimulation (SNS), deep brain stimulation (DBS), transcutaneous stimulation, peripheral nerve stimulation (PNS), or other stimulation, such as peripheral nerve field stimulation (PNFS), cortical stimulation (CS), gastrointestinal stimulation, or any other stimulation therapy capable of treating a condition of patient 14. In some examples, system 10 may be configured where the electrical stimulation includes stimulation parameters to deliver therapy to address a condition of one or more of painful diabetic neuropathy (PDN), peripheral vascular disease (PVD), peripheral artery disease (PAD), complex regional pain syndrome (CRPS), angina pectoris (AP), leg pain, back pain or pelvic pain.

Figure 2A:
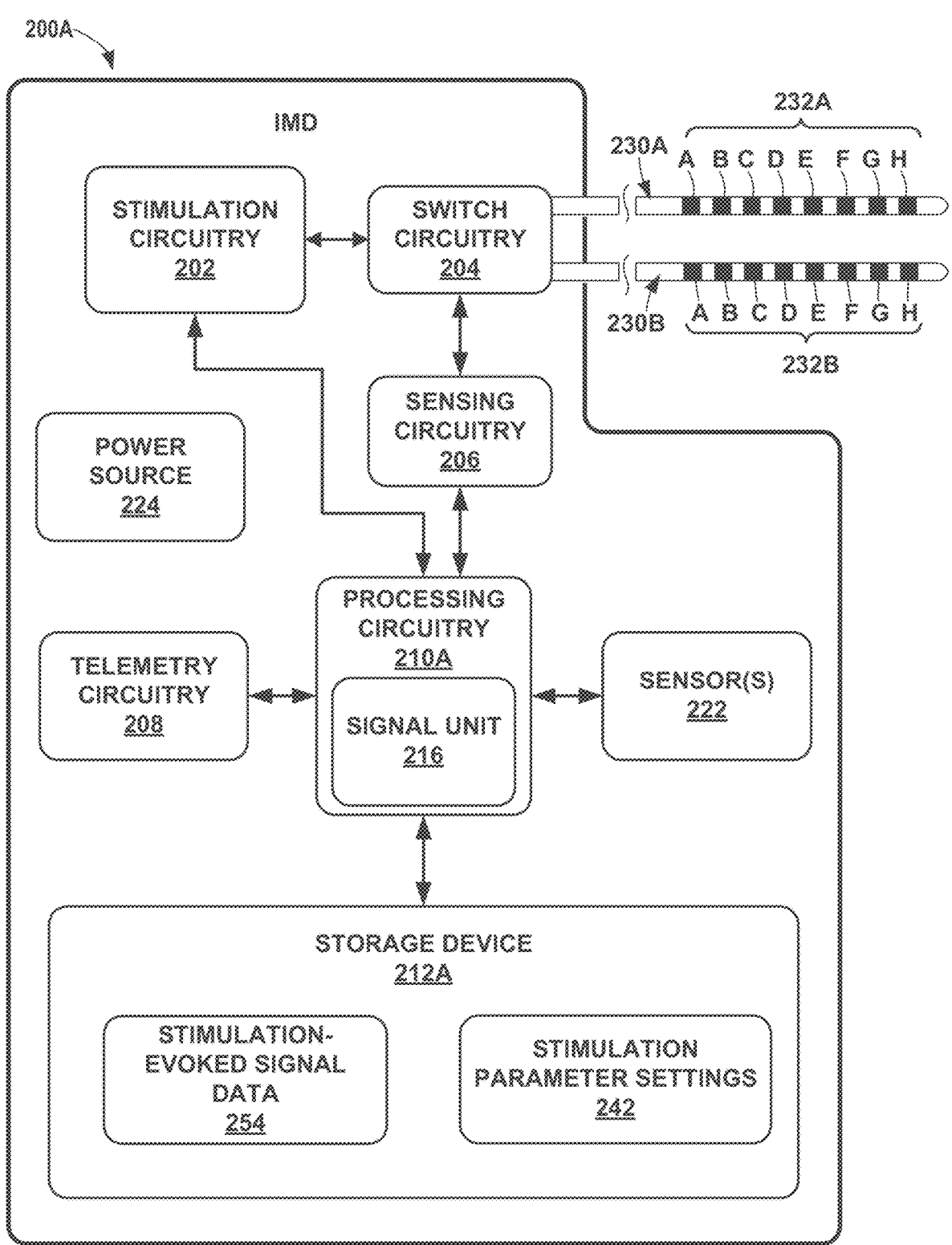
FIG. 2A is a block diagram illustrating an example of an IMD in the form of a neurostimulation device, in accordance with one or more techniques of this disclosure.
Figure 2B:
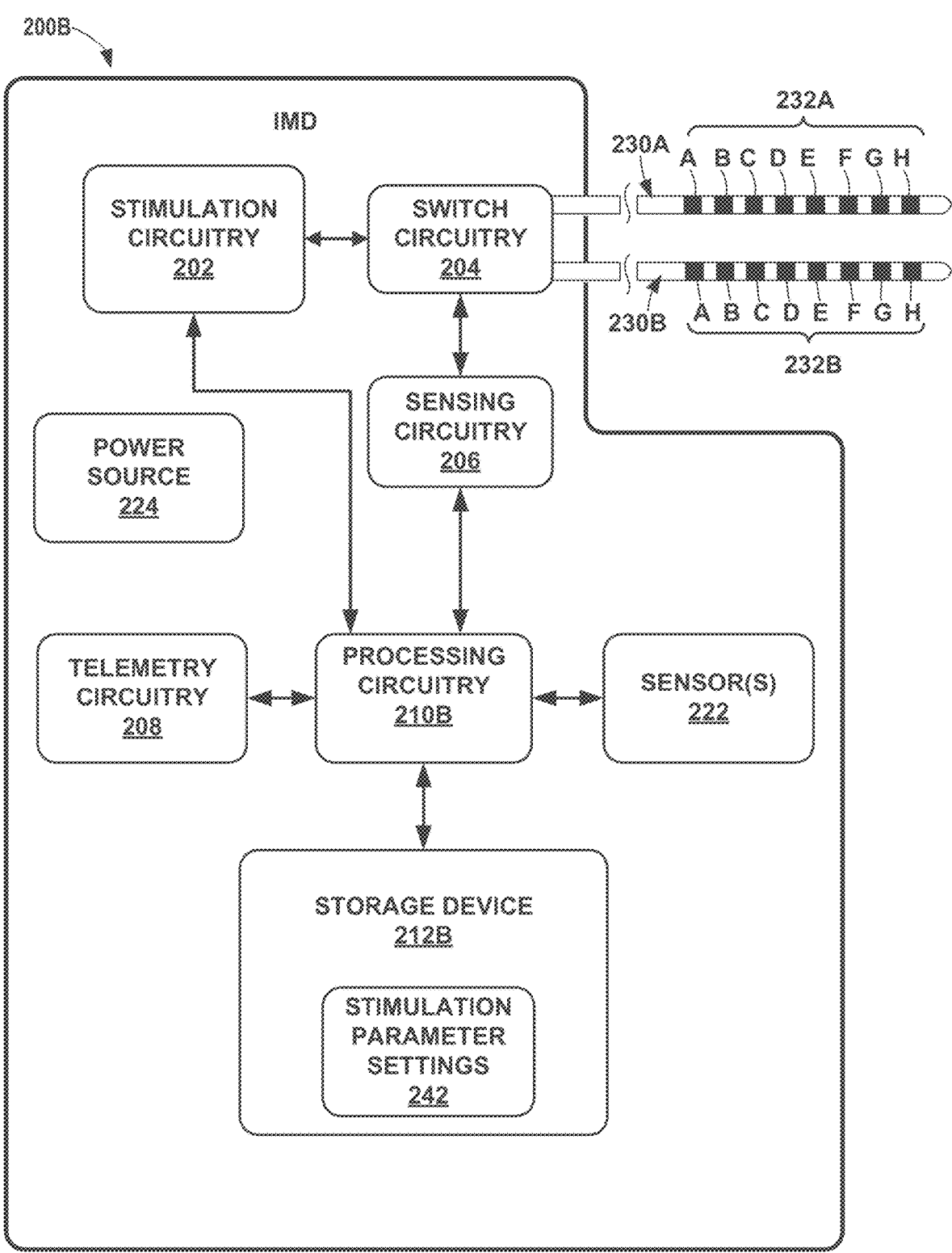
FIG. 2B is a block diagram illustrating an example of an IMD in the form of a neurostimulation device, in accordance with one or more techniques of this disclosure.

FIGS. 2A and 2B are block diagrams illustrating example configurations of components of an IMD 200A and an IMD 200B, respectively, in accordance with one or more techniques of this disclosure. IMD 200A and/or IMD 200B may be an example of IMD 16 of FIG. 1. In the examples shown in FIGS. 2A and 2B, IMD 200A and IMD 200B each include stimulation generation circuitry 202, switch circuitry 204, sensing circuitry 206, telemetry circuitry 208, sensor(s) 222, power source 224, lead 230A carrying electrodes 232A, which may correspond to one of leads 18, 20, 28 and electrodes 19, 21, 29 of FIG. 1, and lead 230B carrying electrodes 232B, which may correspond to another one of leads 18, 20, 28 and electrodes 19, 21, 29 of FIG. 1. In the examples shown in FIG. 2A, IMD 200A includes processing circuitry 210A and storage device 212A, and in the example shown in FIG. 2B, IMD 200B includes processing circuitry 210B and storage device 212B. Processing circuitry 210A and/or 210B may include one or more processors configured to perform various operations of IMD 200A and/or IMD 200B.

In the examples shown in FIGS. 2A and 2B, storage devices 212A and 212B store stimulation parameter settings 242. In addition, as shown in FIG. 2A, storage device 212A may store stimulation-evoked signal data 254 obtained directly or indirectly from one or more electrodes 232 and/or sensors 222, or electrodes 19, 21, 29 and/or sensors 15, 22 (FIG. 1). In this case, IMD 200A of FIG. 2A may process stimulation-evoked signal data 254 and select or adjust stimulation parameter settings 242, including cycling, based on the stimulation-evoked signal data 254.

Stimulation-evoked signal data 254 may include sensed signals from one or more signal sources (e.g., which may be stimulation-evoked and referred to as stimulation-evoked signals) and/or sensed composite stimulation-evoked signals, such as those described above. In some examples, stimulation-evoked signal data 254 may include raw sensed signals from electrodes 232 or sensor(s) 222 and/or amplified, filtered, averaged and/or analog-to-digital converted signals, e.g., via sensing circuitry 206. For example, stimulation-evoked signal data 254 may include a time-varying signal indicative of a response or responses of one or more signal sources (e.g., nerves and/or muscles) to electrical stimulation, such as illustrated and described below with reference to FIGS. 5-9. In some examples, stimulation-evoked signal data 254 may include an averaged signal and/or one or more signal features determined via processing of the signal, e.g., peak/valley detection, peak/valley amplitude, width, and/or area, frequency analysis, digital signal processing, signal latency, and the like. In some examples, stimulation-evoked signal data 254 may include additional information, such as sensor(s) 222 or electrodes 232 settings during sensing of stimulation-evoked signals, a timestamp denoting the date and/or time one or more stimulation-evoked signals are sensed, patient information including a current physiological state of patient 14 physiological measurements of patient 14 at or near the time one or more stimulation-evoked signals are sensed, e.g., heart rate, temperature, blood pressure, patient activity, motion, and/or posture (e.g., patient input and/or measured, such as from a patient smartphone, wearable device, external device 24 or 300, or other device) and the like, or patient input such as a pain level and/or pain score, voiding and/or voiding frequency, patient medical history information, patient age or other demographic information, or any other suitable patient input information.

In one or more examples, such as shown in FIG. 2B, the IMD 200B may not store or receive the stimulation-evoked signal data 254. Instead, external device 24 or another device may directly or indirectly select or adjust stimulation parameter settings based on stimulation-evoked signal data 254 and communicate the selected settings or adjustments to IMD 200B of FIG. 2B. In some examples, stimulation parameter settings 242 may include stimulation parameters (sometimes referred to as "sets of therapy stimulation parameters") for respective different stimulation programs selectable by the clinician or patient for therapy. In some examples, stimulation parameter settings 242 may include one or more recommended parameter settings. In this manner, each stored therapy stimulation program, or set of stimulation parameters, of stimulation parameter settings 242 defines values for a set of electrical stimulation parameters (e.g., a stimulation parameter set), such as electrode combination (selected electrodes and polarities), stimulation current or voltage amplitude, stimulation pulse width, and pulse frequency.

In some examples, stimulation parameter settings 242 may indicate for the stimulation to turn on for a certain period of time, and/or to turn off stimulation for a certain period of time. For example, stimulation parameter settings 242 may further include cycling information indicating when or how long stimulation is turned on and off, e.g., periodically and/or according to a schedule. For example, electrical stimulation may be delivered as a series of electrical stimulation pulses, each pulse being defined by an amplitude, a frequency, a pulse width and/or duration, and an electrical combination (e.g., stimulation pulse parameters). Cycling parameters may define how the series of pulses is delivered. For example, stimulation cycling parameters may include a cycling frequency or period and a duty cycle or ratio of how long electrical stimulation pulses are delivered according to the cycling frequency (an "on-time") to how long electrical stimulation is not delivered (an "off-time"). In other examples, cycling may include a schedule defining the specific times at which electrical stimulation pulses are to be delivered according to specific stimulation pulse parameter settings.

In some examples, stimulation cycling and/or a schedule may include variation over time of any of the electrode combination, amplitude, pulse frequency, pulse width, cycling frequency, and cycling duty cycle, such as a taper in which a parameter is decreased and/or increased. As one specific example of just two parameters, a cycling parameter may include a constant or variable rate of decrease of the amplitude of the pulses and the duty cycle (e.g., a decrease in the on-time/off-time ratio). In some examples, stimulation parameter settings 242 may further include other information and/or limits to other stimulation parameter settings, e.g., such as stimulation pulse or cycling parameter settings limits to deliver electrical stimulation therapy without creating, or to reduce, desensitization of the patient to the electrical stimulation. In some examples, stimulation parameter settings 242 may indicate stimulation to occur at a certain time of day, for example when the patient is typically awake or active, or sleeping. In some examples, stimulation parameter settings 242 relate to when the patient has a certain posture, for example only deliver stimulation when the patient is in a supine position.

Similarly, the sensing may be continuous or periodically, or may be timed or scheduled in response to the aforementioned stimulation cycling and/or scheduling. Additionally, the timing of when to sense for composite signals may be done to optimize longevity or in response to the patient input, clinician input or received physiological data (e.g. other sensor data or previously sensed data).

In some examples, an electrical stimulation signal may comprise electrical stimulation delivered according to one or more electrical stimulation parameter settings 242, e.g., electrical stimulation delivered according to stimulation pulse parameters settings, stimulation cycling parameters settings, and/or any other suitable stimulation parameters settings, information, limits, or conditions.

Stimulation generation circuitry 202 includes electrical stimulation circuitry configured to generate electrical stimulation and generates electrical stimulation pulses selected to alleviate symptoms of one or more diseases, disorders or syndromes. While stimulation pulses are described, stimulation signals may take other forms, such as continuous-time signals (e.g., sine waves) or the like. The electrical stimulation circuitry may reside in an implantable housing, for example of the IMD. Each of leads 230A, 230B may include any number of electrodes 232A, 232B. The electrodes are configured to deliver the electrical stimulation to the patient. In the example of FIGS. 2A and 2B, each set of electrodes 232A, 232B includes eight electrodes A-H. In some examples, the electrodes are arranged in monopolar configurations or bipolar combinations. A bipolar electrode combination may use electrodes carried by the same lead 230A, 230B or different leads. For example, an electrode A of electrodes 232A may be a cathode and an electrode B of electrodes 232A may be an anode, forming a bipolar combination. Switch circuitry 204 may include one or more switch arrays, one or more multiplexers, one or more switches (e.g., a switch matrix or other collection of switches), or other electrical circuitry configured to direct stimulation signals from stimulation generation circuitry 202 to one or more of electrodes 232A, 232B, or directed sensed signals from one or more of electrodes 232A, 232B to sensing circuitry 206. In some examples, each of the electrodes 232A, 232B may be associated with respective regulated current source and sink circuitry to selectively and independently configure the electrode to be a regulated cathode or anode. Stimulation generation circuitry 202 and/ or sensing circuitry 206 also may include sensing circuitry to direct electrical signals sensed at one or more of electrodes 232A, 232B.

Sensing circuitry 206 may be configured to monitor signals from any combination of electrodes 232A, 232B and/or sensor(s) 222. In some examples, sensing circuitry 206 includes one or more amplifiers, filters, and analog-to-digital converters. Sensing circuitry 206 may be used to sense stimulation-evoked and/or physiological signals, such as ECAP signals, EMG signals, and the like. In some examples, sensing circuitry 206 detects ECAP and/or EMG signals from a particular combination of electrodes 232A, 232B. In some cases, the particular combination of electrodes for sensing ECAP and/or EMG signals and/or their composite signal(s) includes different electrodes than a set of electrodes 232A, 232B used to deliver stimulation pulses. Alternatively, in other cases, the particular combination of electrodes used for sensing ECAP and/or EMG signals includes at least one of the same electrodes as a set of electrodes used to deliver stimulation pulses to patient 14. Sensing circuitry 206 may provide signals to an analog-to-digital converter, for conversion into a digital signal for processing, analysis, storage, or output by processing circuitry 210. In some examples, sensing circuitry 206 may sense and/or detect stimulation-evoked signals and/or composite stimulation-evoked signals comprising one or more of an ECAP, an EMG or surface EMG, an MMG, a network excitability, and/or multiple signals of differing signal type evoked by one or more signal sources such as sacral nerves, e.g., dorsal and ventral rami of sacral nerves, pudendal nerves, sciatic nerves, saphenous nerves, nerves in the sacral plexus, pelvic nerves, pelvic plexus nerves, pelvic splanchnic nerves, inferior hypogastric plexus nerves, lumbosacral trunk nerves, e.g., where the lumbosacral trunk joins sacral nerves, any sympathetic nerve fibers in the sympathetic chain of any of the above nerves or other nerves, muscles such as an external anal sphincter muscle, coccygeus muscle, levator ani muscle group, bulbocavernosus and/or bulbospongiosus muscle, gluteal muscles, e.g., gluteal maximus, gluteal medius, and gluteal minimus, perineal muscles, ischiocavernosus muscles, puborectalis muscles, piriformis muscles, or any other muscles.

Sensor(s) 222 may be configured to sense one or more physiological responses of a patient, e.g., patient 14. In some examples, sensor(s) 222 may be substantially the same as sensor(s) 15, 22 described above with reference to FIG. 1. In some examples, sensors 222 may be other sensors located at one or more other positions on patient 14, located at or near one or more muscles and or nerves, or located at positions on patient 14 which may be relatively far from a signal source, e.g., a nerve or muscle.

Telemetry circuitry 208 supports wireless communication between IMD 200A and/or IMD 200B and an external programmer or another computing device under the control of processing circuitry 210. Processing circuitry 210A and/ or 210B of IMD 200A and/or IMD 200B, respectively, may receive, as updates to programs, values for various stimulation parameters such as amplitude and electrode combination, from the external programmer via telemetry circuitry 208. Processing circuitry 210A and/or 210B of IMD 200A and/or IMD 200B, respectively, may store updates to the stimulation parameter settings 242 or any other data in storage device 212. Telemetry circuitry 208 in IMD 200A and/or IMD 200B, as well as telemetry circuits in other devices and systems described herein, such as the external programmer and patient feedback sensing system, may accomplish communication by radiofrequency (RF) communication techniques. In addition, telemetry circuitry 208 may communicate with an external medical device programmer via proximal inductive interaction of IMD 200A and/or IMD 200B with the external programmer, where the external programmer may be one example of external device 24 of FIG. 1. Accordingly, telemetry circuitry 208 may send information to the external programmer on a continuous basis, at periodic intervals, or upon request from IMD 16 and/or external device 24.

Processing circuitry 210A and/or 210B may include one or more processors, such as any one or more of a microprocessor, a controller, a digital signal processor (DSP), an application specific integrated circuit (ASIC), a field-programmable gate array (FPGA), discrete logic circuitry, or any other processing circuitry configured to provide the functions attributed to processing circuitry 210A and/or 210B herein may be embodied as firmware, hardware, software or any combination thereof. Processing circuitry 210A and/or 210B controls stimulation generation circuitry 202 to generate stimulation signals according to stimulation parameter settings 242. In some examples, processing circuitry 210A and/or 210B may execute other instructions stored in storage device 212A and/or 212B, respectively, to apply stimulation parameters specified by one or more of programs, such as electrode combination or configuration, electrode polarity, amplitude, pulse width, pulse shape, pulse frequency or pulse rate, or cycling of each of the stimulation signals.

In the illustrated example of FIG. 2A, processing circuitry 210A includes a signal unit 216 to process stimulation-evoked signals and/or composite stimulation evoked signals. Signal unit 216 may represent an example of a portion of processing circuitry configured to process stimulation-evoked signals and/or composite stimulation-evoked signals received from a sensor, such as electrodes 29, 232 sensor(s) 222 and/or sensor(s) 15, 22, and/or a patient-input device, such as external device 24 or a patient device such as the patient's phone and/or computing device. In the example of FIG. 2B, the processing of stimulation-evoked signals and/or composite stimulation-evoked signals occurs in a device other than IMD 200B. Referring again to FIG. 2A, the signal unit 216, discussed further below, receives information regarding stimulation-evoked signals and/or composite stimulation-evoked signals, such as information relating to sensed and/or received stimulation-evoked signals and/or composite stimulation-evoked signals associated with the efficacy of the electrical stimulation therapy, and controls the electrical stimulation circuitry 202 to deliver the electrical stimulation to the patient based on the received stimulation-evoked signals and/or composite stimulation-evoked signals, where the indications of the received stimulation-evoked signals and/or composite stimulation-evoked signals may be stored in a storage device. Processing circuitry 210A and/or 210B also controls stimulation generation circuitry 202 to generate and apply the stimulation signals to selected combinations of electrodes 232A, 232B. In some examples, stimulation generation circuitry 202 includes a switch circuit (instead of, or in addition to, switch circuitry 204) that may couple stimulation signals to selected conductors within leads 230, which, in turn, deliver the stimulation signals across selected electrodes 232A, 232B. Such a switch circuit may selectively couple stimulation energy to selected electrodes 232A, 232B and to selectively sense stimulation-evoked signals and/or composite stimulation-evoked signals of a sacral nerve or muscles of the patient with selected electrodes 232A, 232B. In other examples, however, stimulation generation circuitry 202 does not include a switch circuit and switch circuitry 204 does not interface between stimulation generation circuitry 202 and electrodes 232A, 232B. In these examples, stimulation generation circuitry 202 may include a plurality of pairs of current sources and current sinks, each connected to a respective electrode of electrodes 232A, 232B. In other words, in these examples, each of electrodes 232A, 232B is independently controlled via its own stimulation circuit (e.g., via a combination of a regulated current source and sink), as opposed to switching stimulation signals between different electrodes of electrodes 232A, 232B.

Storage device 212A and/or 212B may be configured to store information within IMD 200A and/or 200B, respectively, during operation. Storage device 212A and/or 212B may include a computer-readable storage medium or computer-readable storage device. In some examples, storage device 212A and/or 212B includes one or more of a short-term memory or a long-term memory. Storage device 212A and/or 212B may include, for example, random access memories (RAM), dynamic random access memories (DRAM), static random access memories (SRAM), magnetic discs, optical discs, flash memories, or forms of electrically programmable memories (EPROM) or electrically erasable and programmable memories (EEPROM). In some examples, storage device 212A and/or 212B is used to store data indicative of instructions, e.g., for execution by processing circuitry 210A and/or 210B, respectively. As discussed above, storage device 212A and/or 212B is configured to store stimulation parameter settings 242.

Power source 224 is configured to deliver operating power to the components of IMD 200A and/or 200B. Power source 224 may include a battery and a power generation circuit to produce the operating power. In some examples, the battery is rechargeable to allow extended operation. In some examples, recharging is accomplished through proximal inductive interaction between an external charger and an inductive charging coil within IMD 200A and/or 200B. Power source 224 may include any one or more of a plurality of different battery types, such as nickel cadmium batteries and lithium ion batteries.

In some examples as shown in FIG. 2A, the processing circuitry 210A of the IMD 200A directs delivery of electrical stimulation by the electrodes 232A, 232B of leads 230A, 230B, receives stimulation-evoked signal data and/or information from electrodes 232 and/or sensors 222, and generates output based on the received data and/or information. The signal unit 216 may use stimulation-evoked signals and/or composite stimulation-evoked signals or stimulation-evoked signal data 254 and/or information to develop recommended electrical stimulation parameters or adjustments which are outputted to a user, where the user can use the indications or one or more recommended stimulation parameters to program the IMD 200A, e.g., by selecting or accepting the recommendations as stimulation parameter settings to be used by IMD 200A. For example, a particular cycling and/or a set of stimulation parameters are recommended to a user and presented to the user via the programmer. The user may accept the recommended cycling and/or one or more recommended stimulation parameters, and the programmer programs IMD 200A to implement and deliver stimulation with the selected electrode combination and/or stimulation parameters.

Processing circuitry 210A and/or 210B controls stimulation circuitry 202 to deliver stimulation energy with stimulation parameters specified by one or more stimulation parameter settings 242 stored on storage device 212A and/or 212B and, in the example of FIG. 2A, to collect stimulation-evoked signals pertaining to the stored stimulation parameter settings 242. Processing circuitry 210A and/or 210B collects this stimulation-evoked signal information and/or composite stimulation-evoked signal information by receiving the information via sensing circuitry 206 and/or electrodes 232 or sensors 222. Processing circuitry 210A may also control stimulation circuitry 202 to test different parameter settings and record one or more corresponding stimulation-evoked signals for each selected combination, and test different parameter settings as they compare to one or more sensed stimulation-evoked signals. For example, processing circuitry 210A directs stimulation circuitry 202 to deliver stimulation via a particular cycling and the signal unit 216 collects the corresponding stimulation-evoked signal data 254 from telemetry circuitry 208. The stimulation-evoked signal data 254 for this test may be stored in the storage device 212A. Processing circuitry 210A may adjust the previously tested cycling of the stimulation delivered via the electrode combination to a different cycling and collect the corresponding stimulation-evoked signal data 254 from sensors 222 or electrodes 232 and sensing circuitry 206 in response to stimulation with the adjusted cycling. The stimulation-evoked signal data 254 received for the stimulation at the changed stimulation parameter, such as cycling, would be saved in the storage device 212A and may be output to a user. The processing circuitry 210A may continue to shift the cycling by either increasing or decreasing the cycling frequency and/or cycling duty cycle, and recording the respective stimulation-evoked signal data 254, which is stored on the storage device 212A and the information may be output to a user. While the example of cycling is provided, processing circuitry 210A may direct stimulation circuitry 202 to step through various incremental settings of other stimulation parameters, such as electrode combination or configuration, electrode polarity, amplitude, pulse width, pulse shape, pulse frequency or pulse rate, or cycling and record respective stimulation-evoked signal data 254 for each stepped value. In one or more examples, processing circuitry 210A may direct stimulation circuitry to turn on for a certain period of time, and/or to turn off for a period of time, or to turn on at a certain time of day and record the respective stimulation-evoked signal data 254. Stimulation circuitry 202 may shift more than one stimulation parameter for each test and collect sensed stimulation-evoked signal data 254 for each of the multiple shifted stimulation parameters.

In some examples, the signal unit 216 processes the stimulation-evoked signal information and/or composite stimulation-evoked signal information to perform closed-loop control of the stimulation parameters based on the stimulation-evoked signal information and/or composite stimulation-evoked signal information. The signal unit 216 may store the stimulation-evoked signal information and/or composite stimulation-evoked signal information as stimulation-evoked signal data 254 in storage device 212A. For example, signal unit 216 may select or adjust one or more settings of parameter values, such as electrode combination or configuration, electrode polarity, amplitude, pulse width, pulse shape, pulse frequency or pulse rate, or cycling in response to stimulation-evoked signal information. The stimulation-evoked signal information and/or composite stimulation-evoked signal information may be collected when electrical stimulation is not delivered, e.g., just after electrical stimulation is turned off, or upon delivery of electrical stimulation.

In some examples, the signal unit 216 processes the stimulation-evoked signal information and/or accompanying signal information to determine a confidence interval of the stimulation-evoked signal information. For example, signal unit 216 may determine a variance or variances of the stimulation-evoked signal information and may determine a confidence interval corresponding to the stimulation-evoked signal information. If the stimulation-evoked signal information is relatively highly variable, confidence for the stimulation-evoked signal information may be low, e.g., indicating that a signal-to-noise ratio (SNR) of the stimulation-evoked signal information is low. In some examples, if the confidence and/or SNR of the stimulation-evoked signal information is low, signal unit 216 may process and/or average the stimulation-evoked signal information over a longer period of time to reduce the noise/variance. Correspondingly, IMD 200A and/or 200B, respectively, may then monitor the stimulation-evoked signal information for a longer period of time before, e.g., to determine stimulation parameters that may improve patient symptoms, outcomes, or the like. If signal unit 216 determines a confidence and/or SNR to be low, e.g., below a confidence and/or SNR threshold, IMD 200A and/or 200B may not change or base stimulation parameters on the stimulation-evoked signal information, e.g., default parameter settings and/or values may be used instead. Conversely, if the stimulation-evoked signal information has a relatively low variability, signal unit 216 may determine the confidence for the stimulation-evoked signal information to be relatively high, e.g., indicating a relatively high SNR of the stimulation-evoked signal information. IMD 200A and/or 200B may then operate on a pulse-by-pulse basis, e.g., delivering changes to stimulation parameters and/or sensing stimulation-evoked signal information more frequently, and signal unit 216 may extract features from the stimulation-evoked signal information over shorter periods of time and/or more frequently.

In some examples, the processing circuitry 210A and/or 21B of the IMD 200A and/or 210B, respectively, directs delivery of electrical stimulation of the electrodes 232A, 232B (together electrodes 232), and receives information relating to one or more stimulation-evoked signal(s) from one or more sensors 222 or electrodes 232 either directly (e.g., in the case of processing circuitry 210A) or via external controller (e.g., in the case of processing circuitry 210B), and controls the delivery of electrical stimulation of the electrodes 232A, 232B based on the received stimulation-evoked signal information in a closed loop setting. The stimulation-evoked signal information may be received via the telemetry circuitry 208 either directly or indirectly from sensor(s) 15 (FIG. 1) and/or sensor(s) 222 or electrodes 232. In an example, the IMD 200A and/or IMD 200B may receive the stimulation-evoked signal information from an intermediate device other than sensor(s) 15 and/or sensor(s) 222 or electrodes 232, such as external device 24.

Figure 3:
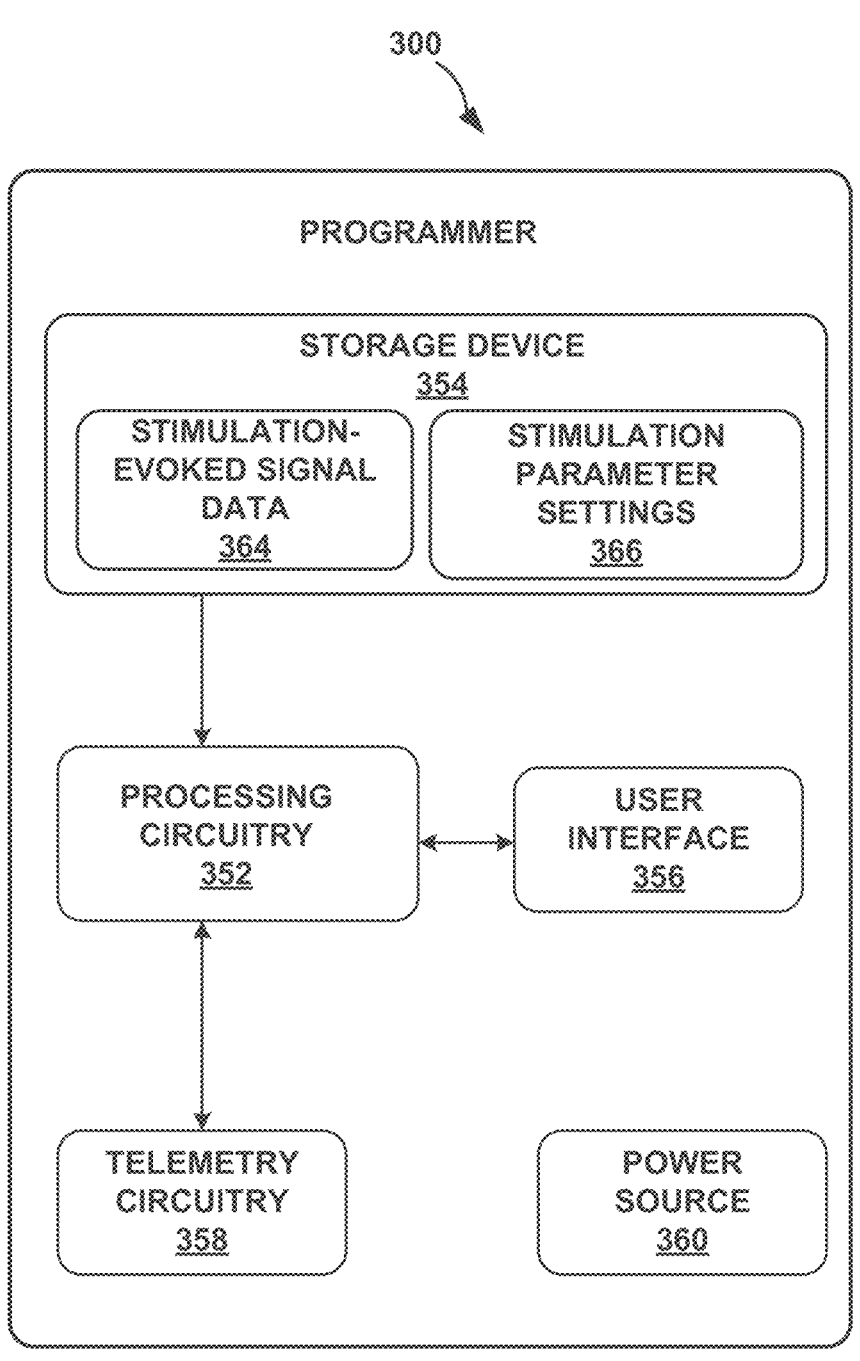
FIG. 3 is a block diagram illustrating an example of an external programmer suitable for use with the IMD of FIG. 2, in accordance with one or more techniques of this disclosure.

FIG. 3 is a block diagram illustrating an example configuration of components of an example external programmer 300. External programmer 300 may be an example of external device 24 of FIG. 1. Although external programmer 300 may generally be described as a handheld device, such as a tablet computer or smartphone-like device, external programmer 300 may be a larger portable device, such as a laptop computer, or a more stationary device, such as a desktop computer. In addition, in other examples, external programmer 300 may be included as part of an external charging device or include the functionality of an external charging device, e.g., to recharge a battery or batteries associated with IMD 200. As illustrated in FIG. 3, external programmer 300 may include processing circuitry 352, storage device 354, user interface 356, telemetry circuitry 358, and power source 360. In some examples, storage device 354 may store instructions that, when executed by processing circuitry 352, cause processing circuitry 352 and external programmer 300 to provide the functionality ascribed to external programmer 300 throughout this disclosure. Each of these components, circuitry, or modules, may include electrical circuitry that is configured to perform some, or all of the functionality described herein. For example, processing circuitry 352 may include processing circuitry configured to perform the processes discussed with respect to processing circuitry 352.

In general, external programmer 300 includes any suitable arrangement of hardware, alone or in combination with software and/or firmware, to perform the techniques attributed to external programmer 300, and processing circuitry 352, user interface 356, and telemetry circuitry 358 of external programmer 300. In various examples, processing circuitry 352, telemetry circuitry 358, or other circuitry of external programmer 300 may include one or more processors, such as one or more microprocessors, DSPs, ASICs, FPGAs, or any other equivalent integrated or discrete logic circuitry, as well as any combinations of such components. External programmer 300 also, in various examples, may include a storage device 354, such as RAM, ROM, PROM, EPROM, EEPROM, flash memory, a hard disk, a CD-ROM, including executable instructions for causing the one or more processors to perform the actions attributed to them. Moreover, although processing circuitry 352 and telemetry circuitry 358 are described as separate modules, in some examples, processing circuitry 352 and telemetry circuitry 358 are functionally integrated. In some examples, processing circuitry 352, telemetry circuitry 358 or other circuitry of external programmer 300 may correspond to individual hardware units, such as ASICs, DSPs, FPGAs, or other hardware units.

The processing circuitry 352 is configured to direct delivery of electrical stimulation, receive information relating to one or more stimulation-evoked signal(s). In some examples, the processing circuitry 352 is configured to control the electrical stimulation circuitry to deliver the electrical stimulation based on the received stimulation-evoked signal information in a closed loop basis by directing the IMD to use particular stimulation parameters.

In some examples, storage device 354 may include instructions that cause processing circuitry 352 to obtain a parameter set from memory or receive user input and send a corresponding command to IMD 200, or instructions for any other functionality. In addition, storage device 354 may include a plurality of programs, where each program includes a parameter set that defines therapy stimulation or control stimulation. Storage device 354 may also store data received from a medical device (e.g., IMD 16) and/or a remote sensing device. For example, storage device 354 may store data recorded at a sensing module of the medical device, and storage device 354 may also store data from one or more sensors of the medical device. In an example, storage device 354 may store data recorded at a remote sensing device such as one or more stimulation-evoked signal sensed by one or more sensors.

User interface 356 may include a button or keypad, lights, a speaker for voice commands, a display, such as a liquid crystal (LCD), light-emitting diode (LED), or organic light-emitting diode (OLED). In some examples, the display includes a touch screen. User interface 356 may be configured to display any information related to the delivery of electrical stimulation including output, for example, information based on one or more stimulation-evoked signal. User interface 356 may also receive user input (e.g., indication of when the patient perceives stimulation, or a pain score perceived by the patient upon delivery of stimulation) via user interface 356. The user input may be, for example, in the form of pressing a button on a keypad or selecting an icon from a touch screen. The input may request starting or stopping electrical stimulation, the input may request a new electrode combination or a change to an existing electrode combination, or the input may request some other change to the delivery of electrical stimulation, such as a change in electrode combination or configuration, electrode polarity, amplitude, pulse width, pulse shape, pulse frequency or pulse rate, or cycling.

Telemetry circuitry 358 may support wireless communication between the medical device and external programmer 300 under the control of processing circuitry 352. Telemetry circuitry 358 may also be configured to communicate with another computing device via wireless communication techniques, or direct communication through a wired connection. In some examples, telemetry circuitry 358 provides wireless communication via an RF or proximal inductive medium. In some examples, telemetry circuitry 358 includes an antenna, which may take on a variety of forms, such as an internal or external antenna.

Examples of local wireless communication techniques that may be employed to facilitate communication between external programmer 300 and IMD 16 include RF communication according to the 802.11 or Bluetooth® specification sets or other standard or proprietary telemetry protocols. In this manner, other external devices may be capable of communicating with external programmer 300 without needing to establish a secure wireless connection. As described herein, telemetry circuitry 358 may be configured to transmit a spatial electrode movement pattern or other stimulation parameters to IMD 16 for delivery of electrical stimulation therapy.

Power source 360 is configured to deliver operating power to the components of external programmer 300. Power source 360 may include a battery and a power generation circuit to produce the operating power. In some examples, the battery is rechargeable to allow extended operation. Recharging may be accomplished by electrically coupling power source 360 to a cradle or plug that is connected to an alternating current (AC) outlet. In addition, recharging may be accomplished through proximal inductive interaction between an external charger and an inductive charging coil within external programmer 300. In other examples, traditional batteries (e.g., nickel cadmium or lithium ion batteries) may be used. In addition, external programmer 300 may be directly coupled to an alternating current outlet to operate.

In some examples, the external programmer 300 directs delivery of electrical stimulation of an IMD, receives information relating to stimulation-evoked signals and/or composite stimulation-evoked signals, and generates output based on the received information, e.g., for evaluation of efficacy of stimulation parameters and/or to recommend or assist a user in programming stimulation parameters for delivery of electrical stimulation, or used as part of a closed loop control scheme to automatically adjust stimulation parameters using stimulation-evoked signal information and/or composite stimulation-evoked signal information. In one or more examples, the external programmer 300 generates output based on stimulation-evoked signal information, e.g., output which may be used as part of closed loop control, output which may be displayed and used by external programmer 300 to manually control therapy delivery, output which may be used to maintain delivery of the same therapy, output which may be recorded and tracked, or output which may be suitable for any other purpose relating to delivery of electrical stimulation therapy.

Programmer 300 may be a patient programmer or a clinician programmer and receives stimulation-evoked signal information and/or composite stimulation-evoked signal information such as stimulation-evoked signal data 364. Programmer 300 receives stimulation-evoked signal(s) information and allows a user to interact with the processing circuitry 352 via user interface 356 in order to identify efficacious parameter settings, such as cycling and/or one or more other stimulation parameters using the stimulation-evoked signal information. Programmer 300 further assists the user in programming a neurostimulation device by using the stimulation-evoked signal information displayed on the user interface 356. In addition, programmer 300 may be used as part of a closed loop control scheme to automatically adjust stimulation parameters based at least on stimulation-evoked signal information. In some examples, programmer 300 receives stimulation-evoked signal information and/or composite stimulation-evoked signal information such as stimulation-evoked signal data 364 from one or more sensor devices and stores the stimulation-evoked signal data 364 in the storage device 354. In some examples, programmer 300 may be device specifically made to communicate with an IMD, e.g., IMD 16, IMD 200A, IMD 200B, and the like, as part of an electrical stimulation system. In other examples, programmer 300 may be a device configured to interact with an IMD or other device of an electrical stimulation system, e.g., a computing device and/or mobile phone configured to run suitable application software for the electrical stimulation system and configured to communicate with one or more devices, e.g., an IMD, of the electrical stimulation system.

Programmer 300 may be used to determine efficacy of particular parameter settings of the IMD by testing parameter settings and recording one or more stimulation-evoked signal for each parameter setting. For example, programmer 300 may be used to cause the IMD to automatically scan though a plurality of electrode combinations or parameter combinations. Processing circuitry 352 causes the IMD to automatically scan through each of a plurality of parameter combinations, including electrode combinations and parameter combinations. For each combination, the programmer 300 obtains and records one or more corresponding stimulation-evoked signal and/or composite stimulation-evoked signal. In some examples, programmer 300 may be used to cause the IMD to automatically scan through a plurality of electrode combinations or parameter combinations at one or more times, e.g., periodically every hour, day, week, month, year, and/or non-periodically, e.g., according to a schedule or other determination of when to repeat a scan, and obtains and records one or more corresponding stimulation-evoked signal and/or composite stimulation-evoked signal for each scan. In some examples, programmer 300 or another device, e.g., IMD 16, external device 24, server 26, or other device, may compare the recorded stimulation-evoked signal and/or composite stimulation-evoked signal over time.

Alternative to or in addition to the automatic scanning process, the user could manually advance scanning through electrode pairs and/or parameter combinations, for example with an arrow button on user interface 356. In some examples, as the user scans through the electrode pairs or parameter combinations to test and record one or more stimulation-evoked signal for each combination.

Figure 11:
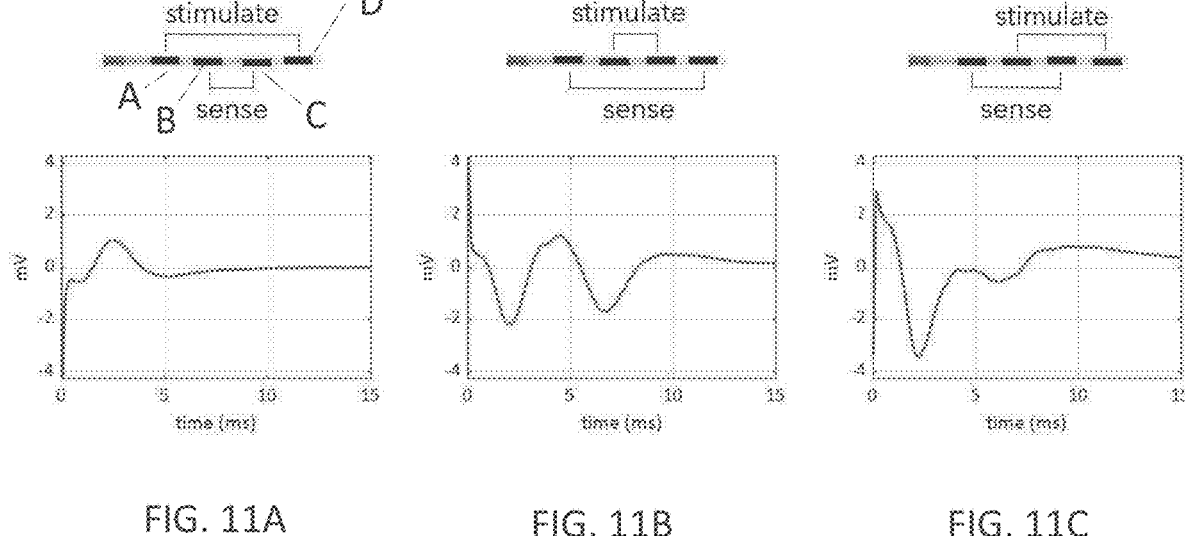
FIGS. 11A-11C illustrates various electrode configurations and respective composite signals, in accordance with one or more techniques of this disclosure.
Figure 12:
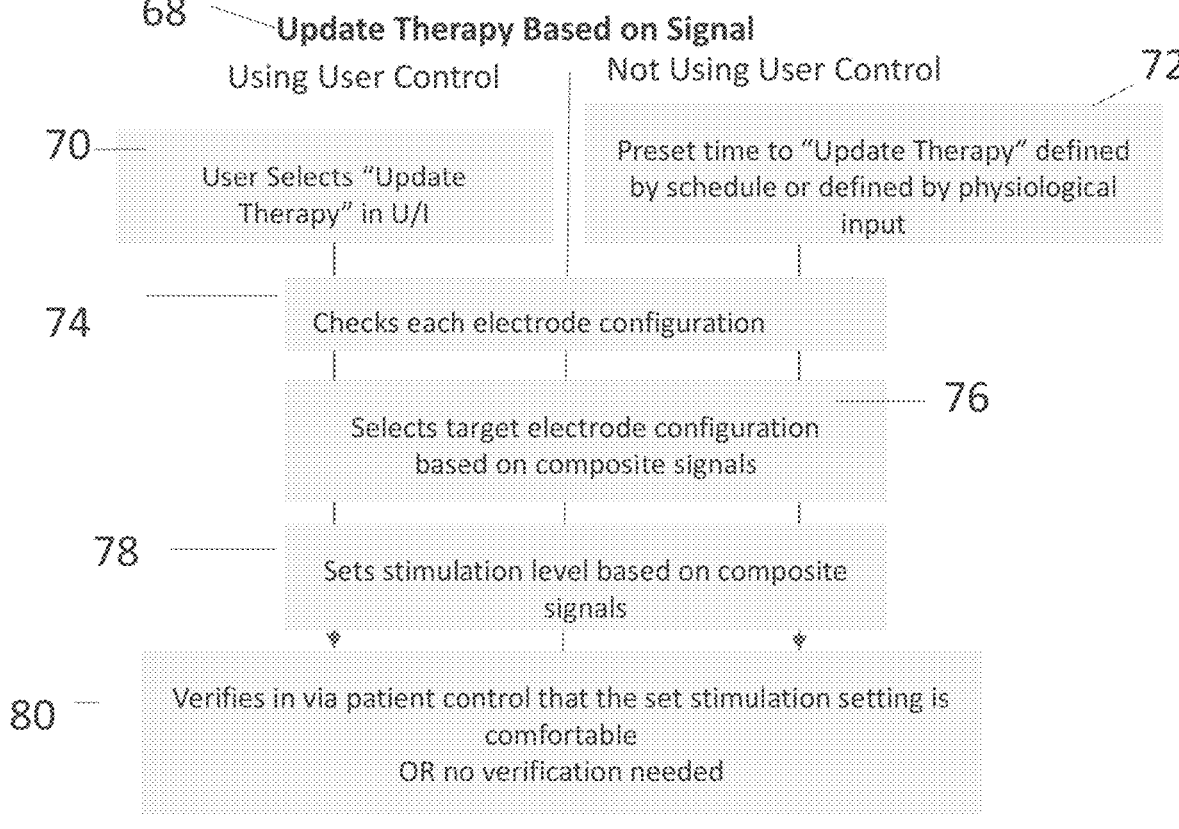
FIG. 12 illustrates a process for updating therapy based on a composite signal, in accordance with one or more techniques of this disclosure.

FIG. 12 illustrates aspects of the disclosure to update therapy 68 based on at least one composite signal either initiated by a clinician (step ##), a patient (step 70) or by a preset time to defined by a schedule set by the patient or the clinician (step 72). In step 70, if a patient would like to initiate an updated therapy informed by the composite signal, the patient can select "update therapy" in a U/I of the patient programmer or other control (e.g. button) aimed to start the process. Alternatively, the implant system may be programmed to update therapy 68 based on a preset time defined by a schedule set by the clinician or the patient or based on other factors (e.g. time of day, patient movement, patient posture) (step 72). Once the update therapy process 68 is started, the following steps may be the same after steps 70, 72. The processing circuitry 352 initiates checks electrode configuration, which may include one or more electrode configurations (step 74). This step 74 may include checking one or more electrode configurations. This step 74 may involve a sweep in which one or more electrode is used to stimulate and either the same and/or one or more other electrode is used to sense a composite signal evoked by the stimulation. The sweep may be sequentially starting at the most distal electrode to the most proximal electrode. The sweep may include electrode configurations that are randomized or that block certain stimulation or sensing electrodes together (similar to the sweeps shown in FIGS. 11A-11C). In some embodiments, step 74 may also include adjusting the stimulation parameters at one or more of the electrode configurations, such as frequency, amplitude, pulse width, etc. In step 76, the processing circuitry 352 assesses the sensed composite signals and selects a target electrode configuration based on the signal. The target electrode configuration may be selected in accordance with techniques described throughout the disclosure (including, e.g. threshold-based selection). In step 79, the processing circuitry 352 sets a stimulation level based on the one or more composite signals. The stimulation level may be the same or different from the existing stimulation level. After the stimulation level is updated, the patient may be prompted to verify the comfort level with the updated stimulation level in step 80. Alternatively, no verification may be needed, e.g. if updated stimulation is below perception thresholds.

Figure 13:
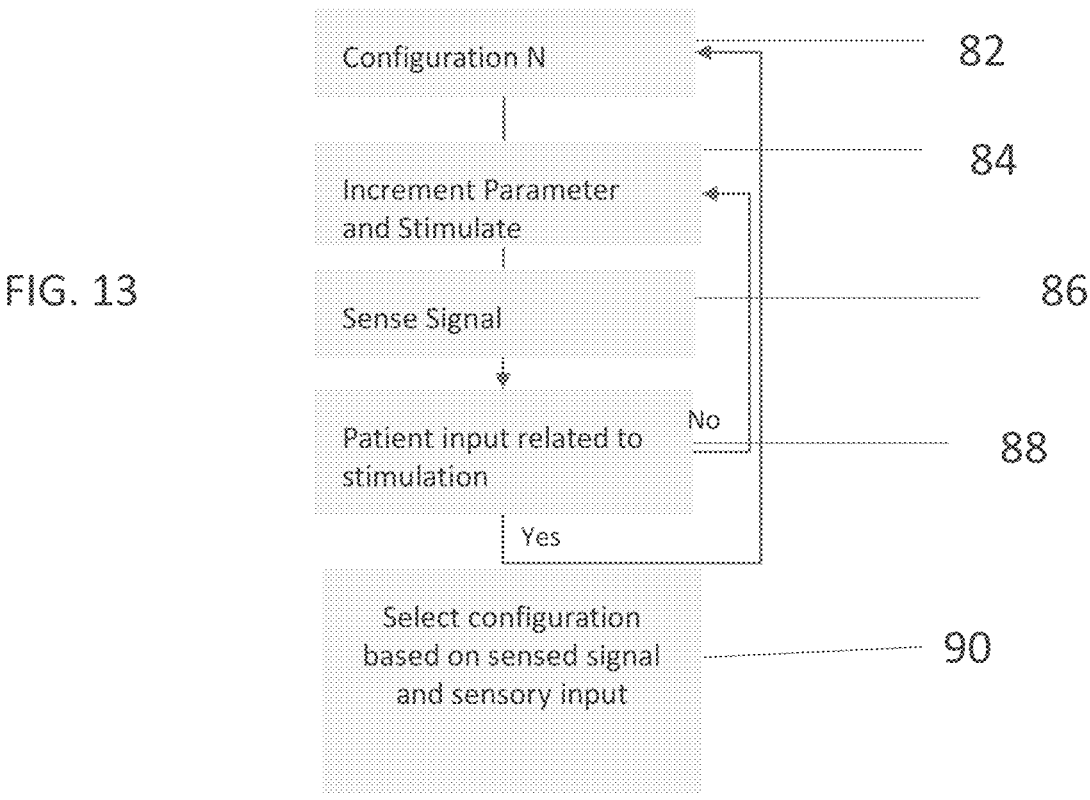
FIG. 13. Illustrates another process for updating therapy based on a composite signal and sensory feedback, in accordance with one or more techniques of this disclosure.

The updated therapy process 68 described in FIG. 12 may also be updated to include sensory information or patient feedback. FIG. 13 illustrates an exemplary process for incorporating sensory information in addition to assessing one or more composite signals to update therapy. As shown in FIG. 13, at least one electrode configurations is selected to assess stimulation at one or more different parameters (Step 82). At the selected electrode configuration, at least one stimulation parameter is adjusted at an increment and stimulation is applied (step 84). In step 86, one or more composite signals are sensed in response to the stimulation. In step 88, a patient is requested to provide input in response to the adjusted stimulation. If the patient inputs negative feedback in step 88, then the process repeats at step 84. In some instances, the negative feedback may include a failure to perceive or feel the adjusted stimulation. If the patient inputs positive feedback in step 88, then the process moves to step 90 and the electrode configuration and stimulation is set based on sensed signal and sensory input. The positive feedback may include an indication from the patient that the adjusted stimulation was perceived.

Processing circuitry 352 controls stimulation circuitry 202 to deliver stimulation energy with stimulation parameters specified by one or more stimulation parameter settings 366 stored on storage device 354, and to collect stimulation-evoked signal information pertaining to the stored stimulation parameter settings 366. Processing circuitry 352 may also control stimulation circuitry 202 to test different parameter settings and record one or more corresponding stimulation-evoked signal for each selected combination, and test different parameter settings as they compare to one or more stimulation-evoked signal. For example, processing circuitry 352 directs stimulation circuitry 202 to deliver stimulation with a particular cycling and one or more stimulation-evoked signal is collected from telemetry circuitry 358. The stimulation-evoked signal data 364 for this test may be stored in the storage device 354.

Processing circuitry 352 may be configured to shift the previously tested cycling to a different cycling and collect one or more corresponding stimulation-evoked signal. The one or more stimulation-evoked signal received and in response to the stimulation at the changed stimulation parameter, in this example cycling, would be saved in the storage device 354. The processing circuitry 352 may continue to shift the cycling by either increasing or decreasing the cycling (e.g., the cycling frequency and/or cycling duty cycle), and record the respective one or more stimulation-evoked signal, which are stored on the storage device 354 and the information is output, e.g., to a different device for processing and/or via user interface 356. While the example of cycling is provided, processing circuitry 352 may direct stimulation circuitry to step through various incremental settings of other stimulation parameters, such as stimulation amplitude, stimulation pulse width, or stimulation frequency, and record the respective stimulation-evoked signal information for each stepped value. Stimulation circuitry 202 may shift more than one stimulation parameter for each test and collect stimulation-evoked signal information for the multiple shifted stimulation parameters.

In some examples, the processing circuitry 352 of programmer 300 directs delivery of electrical stimulation of the electrodes 232A, 232B, and receives information relating to stimulation-evoked signal, and controls the delivery of electrical stimulation of the electrodes 232A, 232B based on the received stimulation-evoked signal information in a closed loop setting. The stimulation-evoked signal information may be received via the telemetry circuitry 358 either directly or indirectly from sensor(s) 222 or electrodes 232 and/or a patient-input device.

The architecture of external programmer 300 illustrated in FIG. 3 is shown as an example. The techniques as set forth in this disclosure may be implemented in the example external programmer 300 of FIG. 3, as well as other types of systems not described specifically herein. Nothing in this disclosure should be construed so as to limit the techniques of this disclosure to the example architecture illustrated by FIG. 3.

Figure 4A:
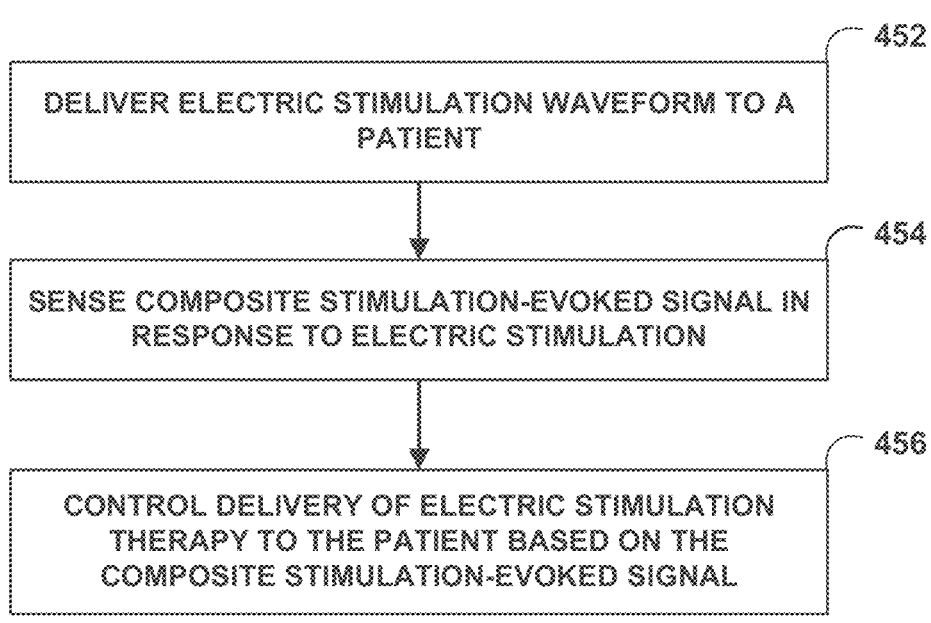
FIG. 4A is a flow diagram illustrating an example method of controlling delivery of electrical stimulation therapy, in accordance with one or more techniques of this disclosure.

FIG. 4A is a flow diagram illustrating an example method of controlling delivery of electrical stimulation therapy, in accordance with one or more techniques of this disclosure. Although FIG. 4A is discussed using IMD 200A of FIG. 2A and external programmer 300 of FIG. 3, it is to be understood that the methods discussed herein may include and/or utilize other systems and methods in other examples.

IMD 200A may deliver one or more electrical stimulation signal to a patient (452). For example, processing circuitry 210A may control stimulation circuitry 202 to deliver stimulation energy via electrodes 232A, 232B with stimulation parameters specified by one or more stimulation parameter settings 242 stored on storage device. In some examples, the electrical stimulation signal may be delivered to one or more of a sacral nerve, a saphenous nerve, a sciatic nerve, a tibial nerve, or a pudendal nerve in any combination. In other examples, the electrical stimulation signal may be delivered to any other nerve or muscle, any portion of the patient's brain, any organ of the patient, or any other tissue of the patient.

In some examples, delivering the one or more stimulation signal to the patient comprises delivering one or more stimulation signal having one or more of non-equal pulse amplitudes, non-equal pulse durations, or non-equal pulse frequencies.

Sensing circuitry 206, via electrodes 232, and/or sensor(s) 222 may sense a composite stimulation-evoked signal comprising a composite of signals generated by one or more signal sources in response to the one or more electrical stimulation signal (454). For example, a composite stimulation-evoked signal sensed by sensing circuitry 206 and/or sensor(s) 222 or electrodes 232 may be a composite of a plurality of stimulation-evoked signals, each of which may originate from a different signal source (e.g., muscle, nerve, etc.), each of which may originate at the same time or at a different time, and each of which may have the same or different duration. For example, processing circuitry 210A may control stimulation circuitry 202, telemetry circuitry, and/or sensing circuitry 206 and/or sensor(s) 222 or electrodes 232 to collect stimulation-evoked signal information, e.g., stimulation-evoked signal data 254. Processing circuitry 210A may store received stimulation-evoked signal data 254 in storage device 212A. In some examples, IMD 200A may receive stimulation-evoked signal(s) as one or more of physiological signals. For example, IMD 200A may receive one or more ECAP, EMG, MMG, and the like.

In some examples, the two or more signal sources may comprise two or more muscles, nerves, or combinations thereof. In some examples, at least one of the two or more signal sources are located relatively far from the sensor capturing the stimulation-evoked signal(s). For example, at least one of the one or more signal source may be least 5 millimeters (mm) from electrodes 232 and/or a sensor 222, at least 10 mm from electrodes 232 and/or a sensor 222, at least 100 mm from electrodes 232 and/or a sensor 222, at least 200 mm from electrodes 232 and/or a sensor 222, at least 1 meter from electrodes 232 and/or a sensor 222, or any other distance within patient 14 from electrodes 232 and/or a sensor 222. In another example at least one of the signal sources is less than 20 mm away or less than 10 mm away from the electrodes 232 and/or sensor 222. As a result, stimulation-evoked signals from the two or more signal sources and captured as composite stimulation-evoked signals may arrive at the electrodes 232 and/or a sensor 222 at different times, e.g., there may be a signal capture time delay between the signals from each source being captured by electrodes 232 and/or a sensor 222. Additionally, the one or more signal sources may have different response times, e.g., differing time delays between electrical stimulation beginning or ending and the initiation of a response. As a result, there may be a signal capture time delay because of the differing response time delays, and/or the signal capture delay may be a combination of the different distances and different response times of the two or more signal sources. In some examples, the composite stimulation-evoked signal that includes stimulation-evoked signals from the two or more signal sources may have a relative long duration, e.g., at least 5 ms, at least 10 ms, at least 20 ms, etc. For example, the composite stimulation-evoked signal may comprise an ECAP signal generated relatively quickly after delivery of electrical stimulation signals, e.g., within 0.5 ms, 1 ms, within 3 ms, within 5 ms, within 10 ms and an EMG signal generated relatively slowly after delivery of electrical stimulation signals, e.g., after 5 ms, or after 3 ms, or after 1 ms. In some examples, the composite stimulation-evoked signal may comprise signals from multiple signal sources that do not overlap in time. For example, the composite stimulation-evoked signal may comprise an ECAP signal from a signal source relatively close to the sensor and/or electrode followed by an EMG signal or another ECAP signal from the same signal source, or from a different signal source that may be relatively far from the sensor and/or electrode, e.g., such that the ECAP from the close signal source is no longer present while the EMG signal and/or ECAP from the more distant signal source are received by the sensor and/or electrode. In some examples, the composite stimulation-evoked signal may have an amplitude of one or more peaks that are greater than 1 millivolt (mV), or greater than 0.1 mV, or greater than 0.01 mV, or greater than 0.001 mV.

In some examples, processing circuitry 210A may receive one or more sensed stimulation-evoked signals, e.g., a stimulation-evoked signal from a signal source and/or a composite stimulation-evoked signal. For example, processing circuitry 210A may receive one or more composite stimulation-evoked signals from sensing circuitry 206, and may store the one or more composite stimulation-evoked signal and any other information relating to the one or more composite stimulation-evoked signal in a storage device, e.g., as stimulation-evoked signal data 254. For example, processing circuitry 210A may store a stimulation-evoked signal as digital information representing a signal amplitude at a plurality of times. In some examples, the signal amplitude may represent a sensed voltage, current, capacitance, or inductance, e.g., for an electrical signal sensor. In some examples, the signal amplitude may represent a displacement, a pressure, accelerometer data, a sound, e.g., such as an MMG signal. In still other examples, the signal amplitude may represent any measurable physical quantity representing a physiological response of a signal source (e.g., muscle, nerve, and the like) to electrical stimulation.

A user, clinician, and/or IMD 200A may control delivery of electrical stimulation therapy to the patient based on the composite stimulation-evoked signal (456). For example, a user and/or clinician may adjust the placement and/or positioning of leads 230A, 230B based on proposed changes output by the machine learning and/or artificial intelligence model, the proposed changes being based on one or more features of the composite stimulation-evoked signal. In some examples, a user or clinician may manually change or adjust, or processing circuitry 210A may automatically change or adjust, one or more stimulation parameter setting 242 based on proposed changes output by the machine learning and/or artificial intelligence model, the proposed changes being based on one or more features of the composite stimulation-evoked signal, e.g., for future electrical stimulation. In some examples, a user, clinician, and/or processing circuitry 210A may determine whether the current electrical stimulation is effective based on output by comparing the output to a threshold based on one or more features of the composite stimulation-evoked signal, or by the machine learning and/or artificial intelligence model, the output being based on one or more features of the composite stimulation-evoked signal. If the user, clinician, and/or processing circuitry 210A determines that therapy is effective, proposed changes may be bypassed and/or not implemented. If the user, clinician, and/or processing circuitry 210A determines that therapy is not effective, the user, clinician, and/or processing circuitry 210A may change and/or adjust lead placement and/or positioning and/or one or more stimulation parameter setting 242 based on something other than the composite stimulation-evoked signal(s), e.g., according to a predetermined schedule of changes or some other basis.

Figure 4B:
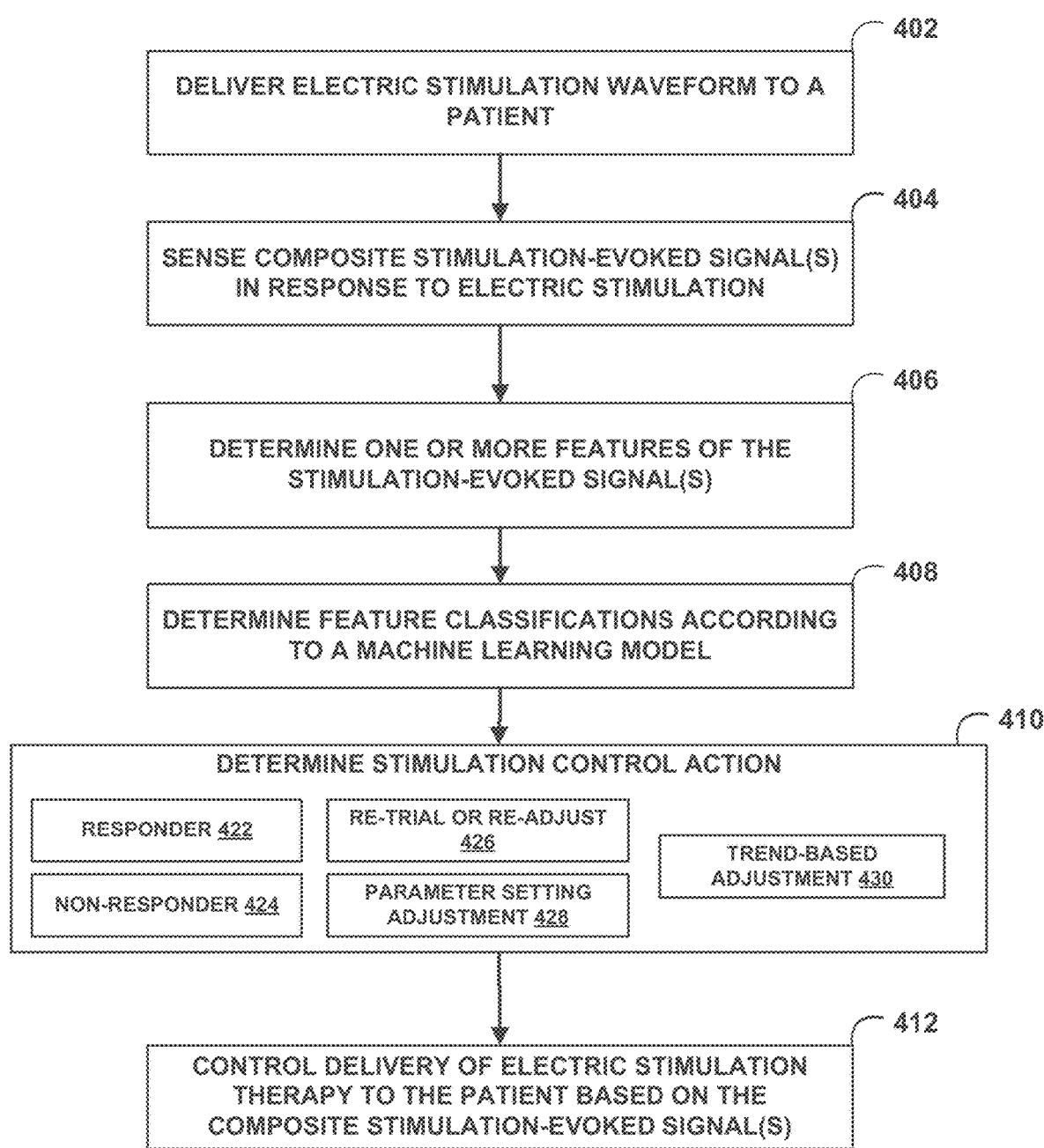
FIG. 4B is a flow diagram illustrating an example method of controlling delivery of electrical stimulation therapy, in accordance with one or more techniques of this disclosure.

FIG. 4B is a flow diagram illustrating an example method of controlling delivery of electrical stimulation therapy, in accordance with one or more techniques of this disclosure. Although FIG. 4B is discussed using IMD 200A of FIG. 2A and external programmer 300 of FIG. 3, it is to be understood that the methods discussed herein may include and/or utilize other systems and methods in other examples.

IMD 200A may deliver one or more electrical stimulation signal to a patient (402). For example, processing circuitry 210A may control stimulation circuitry 202 to deliver stimulation energy via electrodes 232A, 232B with stimulation parameters specified by one or more stimulation parameter settings 242 stored on storage device. In some examples, the electrical stimulation signal may be delivered to one or more of at least one sacral nerve, at least one saphenous nerve, at least one sciatic nerve, at least one tibial nerve, or at least one pudendal nerve in any combination. In other examples, the electrical stimulation signal may be delivered to any other nerve or muscle, any portion of the patient's brain, any organ of the patient, or any other tissue of the patient.

In some examples, delivering the one or more stimulation signal to the patient comprises delivering one or more stimulation signal having one or more of non-equal pulse amplitudes, non-equal pulse durations, non-equal polarity, or non-equal pulse frequencies.

Sensing circuitry 206, via electrodes 232, and/or sensor(s) 222 may sense a composite stimulation-evoked signal comprising a composite of signals generated by two or more signal sources in response to the one or more electrical stimulation signal (404). For example, a composite stimulation-evoked signal sensed by sensing circuitry 206 and/or sensor(s) 222 may be a composite of a plurality of stimulation-evoked signals, each of which may originate from a different signal source (e.g., muscle, nerve, etc.), each of which may originate at the same time or at a different time, and each of which may have the same or different duration. For example, processing circuitry 210A may control stimulation circuitry 202, telemetry circuitry, and/or sensing circuitry 206 and/or sensor(s) 222 or electrodes 232 to collect stimulation-evoked signal information, e.g., stimulation-evoked signal data 254. Processing circuitry 210A may store received stimulation-evoked signal data 254 in storage device 212A. In some examples, IMD 200A may receive stimulation-evoked signal(s) as one or more of physiological signals. For example, IMD 200A may receive one or more ECAP, EMG, MMG, and the like.

In some examples, the one or more signal sources may comprise two or more muscles, nerves, or combinations thereof. In some examples, at least one of the two or more signal sources are located relatively far from the sensor capturing the stimulation-evoked signal(s). For example, at least one of the two or more signal source may be least 5 millimeters (mm) from electrodes 232 and/or a sensor 222, at least 10 mm from electrodes 232 and/or a sensor 222, at least 100 mm from electrodes 232 and/or a sensor 222, at least 200 mm from electrodes 232 and/or a sensor 222, at least 1 meter from electrodes 232 and/or a sensor 222, or any other distance within patient 14 from electrodes 232 and/or a sensor 222. As a result, stimulation-evoked signals from the two or more signal sources and captured as composite stimulation-evoked signals may arrive at the electrodes 232 and/or a sensor 222 at different times, e.g., there may be a signal capture time delay between the signals from each source being captured by electrodes 232 and/or a sensor 222. Additionally, the one or more signal sources may have different response times, e.g., differing time delays between electrical stimulation beginning or ending and the initiation of a response. As a result, there may be a signal capture time delay because of the differing response time delays, and/or the signal capture delay may be a combination of the different distances and different response times of the two or more signal sources. In some examples, the composite stimulation-evoked signal that includes stimulation-evoked signals from the two or more signal sources may have a relatively long duration, e.g., at least 5 ms, at least 10 ms, at least 20 ms, etc. For example, the composite stimulation-evoked signal may comprise an ECAP signal generated relatively quickly after delivery of electrical stimulation signals, e.g., within 10 ms, and an EMG signal generated relatively slowly after delivery of electrical stimulation signals, e.g., after 5 ms, or after 3 ms, or after 1 ms. In some examples, the composite stimulation-evoked signal may comprise signals from multiple signal sources that do not overlap in time. For example, the composite stimulation-evoked signal may comprise an ECAP signal from a signal source relatively close to the sensor and/or electrode followed by an EMG signal or another ECAP signal from the same signal source, or from a different signal source that may be relatively far from the sensor and/or electrode, e.g., such that the ECAP from the close signal source is no longer present while the EMG signal and/or ECAP from the more distant signal source are received by the sensor and/or electrode. In some examples, the composite stimulation-evoked signal may have an amplitude of one or more peaks that are greater than 1 millivolt (mV), or greater than 0.1 mV, greater than 0.01 mV, or greater than 0.001 mV.

In some examples, processing circuitry 210A may receive one or more sensed stimulation-evoked signals, e.g., a stimulation-evoked signal from a signal source and/or a composite stimulation-evoked signal. For example, processing circuitry 210A may receive one or more composite stimulation-evoked signals from sensing circuitry 206, and may store the one or more composite stimulation-evoked signal and any other information relating to the one or more composite stimulation-evoked signal in a storage device, e.g., as stimulation-evoked signal data 254. For example, processing circuitry 210A may store a stimulation-evoked signal as digital information representing a signal amplitude at a plurality of times. In some examples, the signal amplitude may represent a sensed voltage, current, capacitance, or inductance, e.g., for an electrical signal sensor. In some examples, the signal amplitude may represent a displacement, a pressure, accelerometer data, a sound, e.g., such as an MMG signal. In still other examples, the signal amplitude may represent any measurable physical quantity representing a physiological response of a signal source (e.g., muscle, nerve, and the like) to electrical stimulation.

IMD 200A, external programmer 300, or another device such as a computing device, may determine one or more features of the composite stimulation-evoked signal (406). For example, processing circuitry, such as processing circuitry 210A of IMD 200A, or other processing circuitry of another computing device, may process the stimulation-evoked signal data 254 or 354 to determine one or more features. In some examples, processing circuitry 210A may store the determined one or more features in storage device 212A, e.g., as additional stimulation-evoked signal data 254.

For example, processing circuitry 210A may determine one or more features illustrated and described below with reference to FIGS. 5-9. For example, and with reference to FIG. 9, processing circuitry 210A may determine one or more peaks and/or valleys and their corresponding peak/valley amplitudes, areas, widths, and latency relative to a reference time, e.g., time T0, of composite stimulation-evoked signal 902. Processing circuitry 210A may determine one or more times-between-peaks (ΔT) between one or more peaks and/or valleys of composite stimulation-evoked signal 902. Processing circuitry 210A may determine one or more ratios between one or more peak amplitudes, areas, widths, and or times-between-peaks of composite stimulation-evoked signal 902 or a threshold for when the composite stimulation-evoked signal appears. Processing circuitry 210A may further determine a feature based on stimulation-evoked signal 902 crossing one or more amplitude values, e.g., changing to increase above and/or decrease below one or more amplitude thresholds. Processing circuitry 210A may further determine the spectral content and/or a power spectral density of composite stimulation-evoked signal 902, e.g., an amount of one or more frequency components. In some examples, processing circuitry may determine the width of the signal at half of the max amplitude, the root-mean-square (ms) signal value, signal skew, kurtosis, a growth curve, a rate of growth, a neural threshold, an inflection point, or any other suitable signal feature of composite stimulation-evoked signal 902 or ratios of any such features. In certain embodiments, processing circuitry 210A records features based on the distribution of the received composite stimulation-evoked signals across one or more electrodes from one or more sources.

IMD 200A, external programmer 300, or another computing device, may determine one or more classifications of the one or more determined features of the composite stimulation-evoked signal, e.g., via a machine learning and/or artificial intelligence algorithm and/or model (408). The one or more classifications may be used by a machine learning and/or artificial intelligence algorithm and/or model to determine an efficacy of the delivered electrical stimulation signal and/or determine and output proposed changes to electrical stimulation delivery, e.g., changes in stimulation parameter settings 242, adjusting placement and/or positions of leads 230A, 230B, and the like.

IMD 200A, external programmer 300, or another computing device, may determine one or more stimulation control actions (410). For example, the determined one or more stimulation-evoked signal features and determined classifications may be used to adjust electrical stimulation therapy. In some examples, the same or another machine learning and/or artificial intelligence algorithms and/or model, or a different computer program and/or methodology, may predict electrical stimulation efficacy for patient 14 for one or more lead placement/positioning changes and/or electrical stimulation parameters settings 242 changes based on the determined features and classifications, and may determine one or more lead placement/positioning changes and/or electrical stimulation parameters settings 242 changes to improve electrical stimulation therapy.

In some examples, IMD 200A may determine a likelihood of patient 14 responding to therapy, e.g., whether patient 14 may be a responder 422 or non-responder 424. In some examples, IMD 200A may determine patient 14 is a good candidate (responder 422) for a full electrical stimulation treatment, e.g., externally implied or a full implant of an IMD without further electrical stimulation trials. In some examples, IMD 200A may determine that further electrical stimulation trials should be performed (retrial and/or readjust 426) and may determine the corresponding leads 230 placement and electrical stimulation parameters settings 242 for such trials. IMD 200A may determine that patient 14 may not be a good candidate for electrical stimulation (non-responder 424) and electrical stimulation should not be further explored nor should an IMD be implanted.

In some examples, IMD 200A may determine signal features (406) and classifications (408) at a single point in time, e.g., at implanting of an IMD or application of an external electrical stimulation device, the beginning and/or ending of electrical stimulation trials, at a scheduled clinic visit, during an at home electrical stimulation therapy session, and the like. IMD 200A may determine electrical stimulation therapy efficacy based on the determined features and feature classifications, and may further determine improved and/or optimal lead placement/positioning and electrical stimulation parameters settings 242 based on the determined features and feature classifications. In some examples, IMD 200A may further determine improved and/or optimal lead placement/positioning and electrical stimulation parameters settings 242 further based on therapy efficacy and energy use, e.g., energy use and/or battery life of IMD 200A. In certain embodiments, the features of the simulation-evoked signals used for lead placement may be indicative of lead insertion depth, lead insertion trajectory relative to the sacral foramen, lead specific side of the body and sacral level of the foramen for placement.

In some examples, IMD 200A may determine changes of stimulation-evoked signals and/or composite stimulation-evoked signals over time. For example, IMD 200A may determine that one or more features of a stimulation-evoked signal has changed between stimulation-evoked signals collected at two different times. For example, stimulation-evoked signal feature changes may occur during stimulation trials, e.g., the same electrical stimulation may be delivered and one or more signal features may be different in a relatively short period of time encompassing the time over which electrical stimulation trials are performed. In other examples, stimulation-evoked signal feature changes may occur chronically, e.g., over the course of electrical stimulation therapy being delivered to patient 14 at a plurality of different times to treat a chronic condition. In some examples, and a machine learning and/or artificial intelligence algorithm and/or model may compare changes in stimulation-evoked signals at different times and/or the corresponding signal features and may predict future electrical stimulation therapy efficacy. In some examples, a machine learning and/or artificial intelligence algorithm and/or model may determine one or more lead placement/positioning and/or electrical stimulation parameters settings 242 changes to improve electrical stimulation therapy efficacy, e.g., trend-based adjustment 430.

A user, clinician, and/or IMD 200A may control delivery of electrical stimulation therapy to the patient based on the composite stimulation-evoked signal (412). For example, a user and/or clinician may adjust the placement and/or positioning of leads 230A, 230B based on proposed changes output by the machine learning and/or artificial intelligence model, the proposed changes being based on one or more features of the composite stimulation-evoked signal. In some examples, a user or clinician may manually change or adjust, or processing circuitry 210A may automatically change or adjust, one or more stimulation parameter setting 242 based on proposed changes output by the machine learning and/or artificial intelligence model, the proposed changes being based on one or more features of the composite stimulation-evoked signal, e.g., for future electrical stimulation. In some examples, a user, clinician, and/or processing circuitry 210A may determine whether the current electrical stimulation is effective based on output by the machine learning and/or artificial intelligence model, the output being based on one or more features of the composite stimulation-evoked signal. If the user, clinician, and/or processing circuitry 210A determines that therapy is effective, proposed changes may be bypassed and/or not implemented. If the user, clinician, and/or processing circuitry 210A determines that therapy is not effective, the user, clinician, and/or processing circuitry 210A may change and/or adjust lead placement and/or positioning and/or one or more stimulation parameter setting 242 based on something other than the composite stimulation-evoked signal(s), e.g., according to a predetermined schedule of changes or some other basis.

Figure 9:
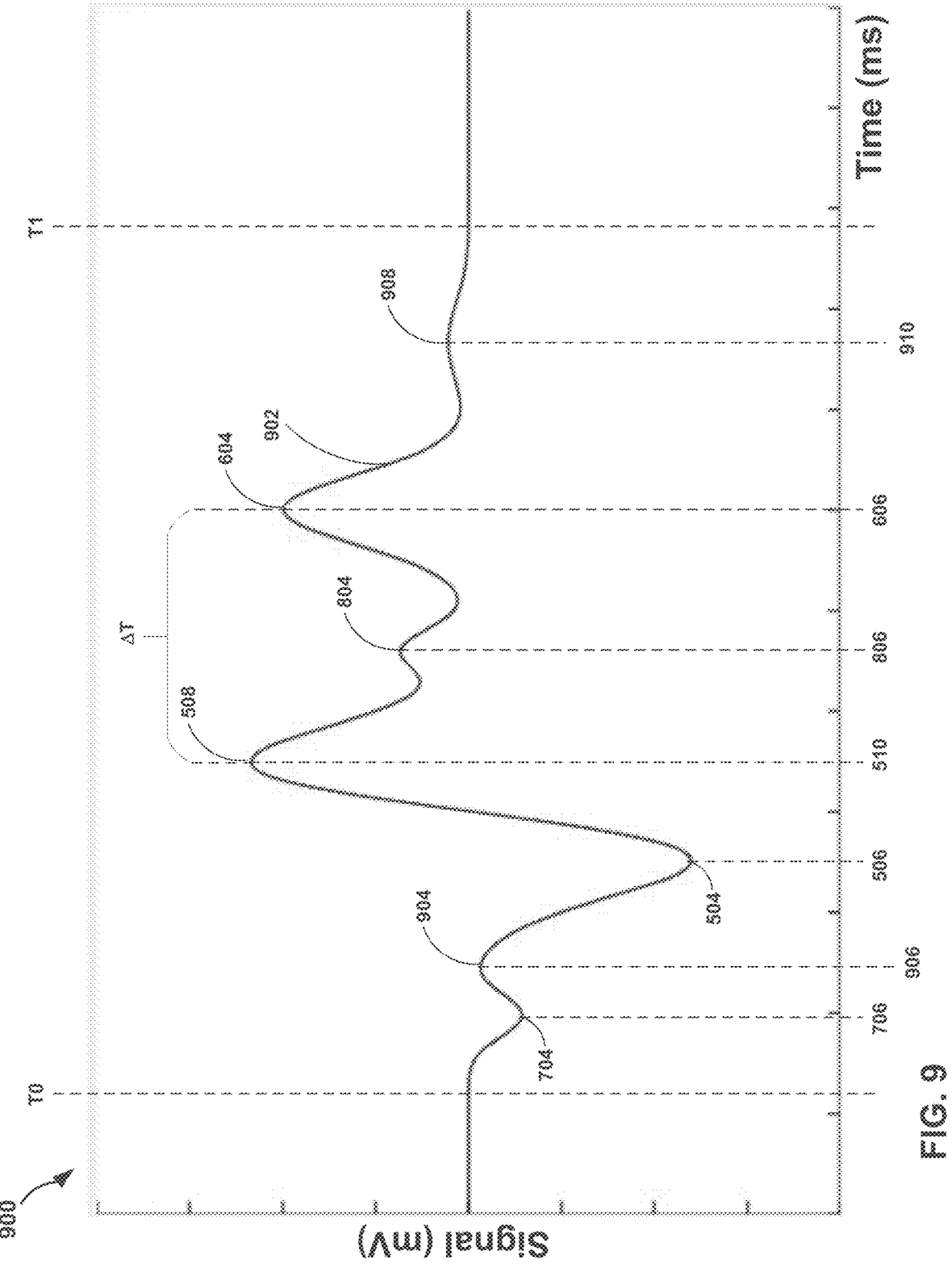
FIG. 9 is a plot of another example composite stimulation-evoked signal, in accordance with one or more techniques of this disclosure.

FIGS. 5-8 are plots of example stimulation-evoked signals and FIG. 9 is an example stimulation-evoked signal or composite stimulation-evoked signal, and are described together below. In the specific examples of FIGS. 5-9 below, each signal plotted represent a voltage amplitude of a circuit including an electrode 232 that varies in time in proportion to a time-varying electric field sensed by the electrode 232. The time-varying field in the examples shown is caused by one or more signal sources, e.g., nerve, muscle, or other tissue, of a patient in response to electrical stimulation. However, FIGS. 5-9 may generally represent one or more other quantities. In some examples, each signal plot may represent an amplitude as a function of time of a sensed quantity over time, the quantity varying in proportion to a physiological response of a signal source. In some examples, the quantity is an amplitude measured by a sensor. For example, the amplitude may be a voltage and/or current that varies in time according to an amplitude of an electric field and/or potential emitted and/or induced by a signal source. In some examples, the amplitude may be a displacement, a pressure, accelerometer data, a sound, e.g., such as an MMG signal. In some examples, composite stimulation-evoked signal 902 described below may be a composite of sensed quantities from a plurality of sources sensed by a plurality of sensors, e.g., combined amplitudes as a function of time from two or more different sensors sensing two or more different quantities from one or more different signal sources that respond to the same electrical stimulation at or near the same time or within a period of time (e.g., a sensing "time window"). In some examples, two sensors may sense two different quantities from the same signal source, e.g., an EMG and an MMG of a muscle response. In other examples, composite stimulation-evoked signal 902 may be a composite of a sensed quantity, e.g., an electric field and/or potential, from a plurality of signal sources sensed by the same sensor, e.g., an electrode 232 sensing a varying electric field that is a superposition of a plurality of electric fields caused by a plurality of signal sources responding to electrical stimulation within a sensing time window.

Figures 5, 6, 7, 8:
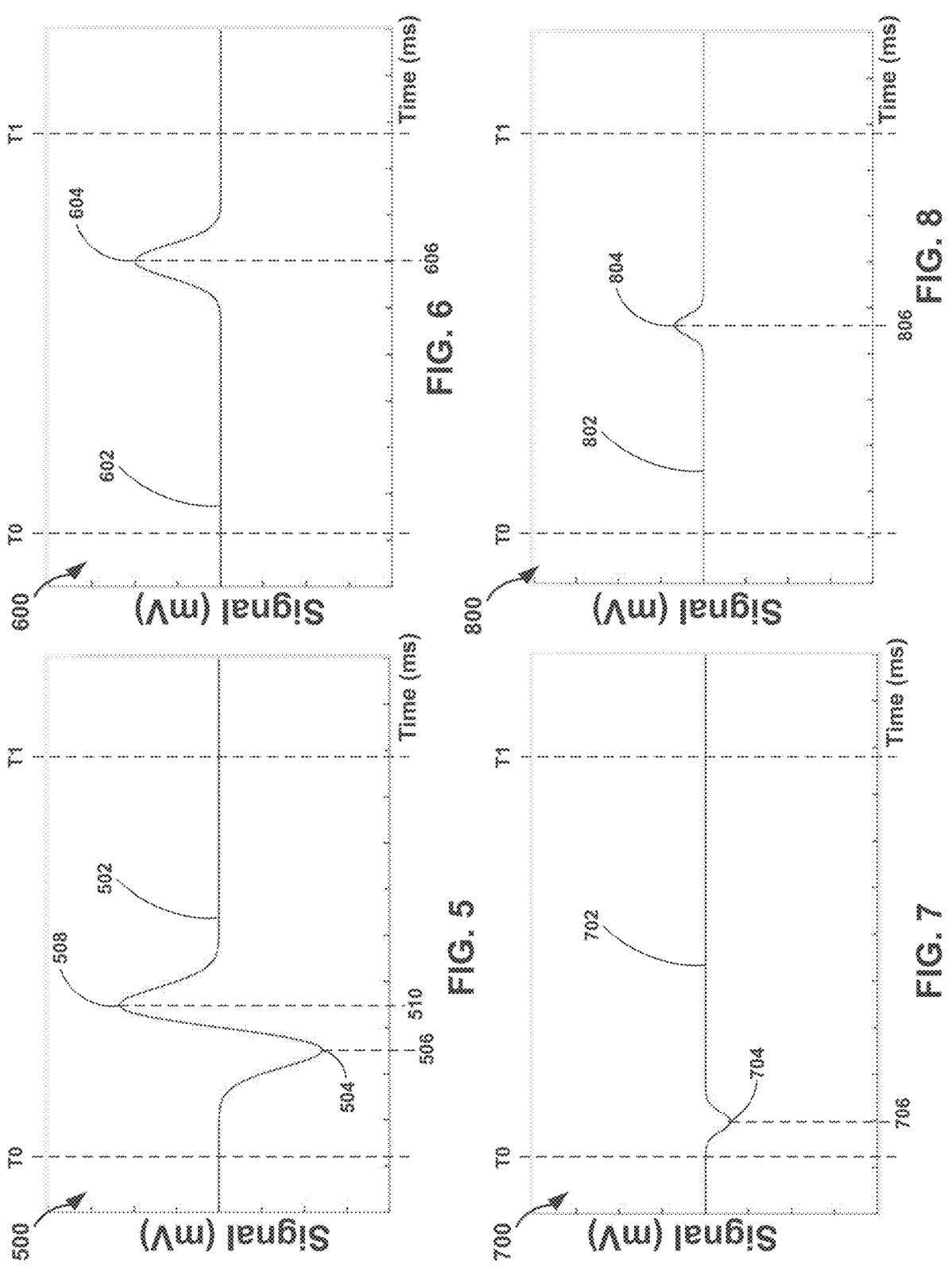
FIG. 5 is a plot of an example stimulation-evoked signal, in accordance with one or more techniques of this disclosure.
FIG. 6 is a plot of another example stimulation-evoked signal, in accordance with one or more techniques of this disclosure.
FIG. 7 is a plot of another example stimulation-evoked signal, in accordance with one or more techniques of this disclosure.
FIG. 8 is a plot of another example stimulation-evoked signal, in accordance with one or more techniques of this disclosure.

FIG. 5 is a plot 500 of an example stimulation-evoked signal 502, in accordance with one or more techniques of this disclosure. In the example shown, signal 502 is a voltage amplitude that varies in time in proportion to a time-varying electric field sensed by an electrode 232, the time-varying electric field caused by a signal source in response to electrical stimulation. In the example shown, time T0 corresponds to a time at which electrical stimulation of a nerve or muscle ceases, e.g., is turned off, and time T1 corresponds to the ending time of the sensing time window, e.g., the sensing time window is the difference between T0 and T1. In some examples, signal 502 may have a signal length in time that is equal to the time window, e.g., the physiological response of the signal source emits a detectable quantity (e.g., electric field) that lasts for the length of the time window. In other examples, the signal length of signal 502 may be less than the time window. Generally, the time window may be chosen based on signal length, e.g., time T0 may be chosen to be the time at which electrical stimulation ceases and time T1 may be chosen based on the time-length of the sensed signal, e.g., any of 502, 602, 702, 802, and/or 902. In the examples of FIGS. 5-9, T1 chosen based on an exemplary time-length of signal 902 and is shown on each of plots 500-900 for reference. In some examples, the length of stimulation-evoked signals 502-902 may be, e.g., 1 ms, 5 ms, 10 ms, 15 ms, 20 ms, 30 ms, or longer. In some examples, the shape, length, and location along the time axis of one or more features of stimulation-evoked signals 502-802 may be different.

In the example shown, signal 502 includes valley 504 (which may be considered a "peak" with a negative amplitude and may be simply referred to as a "peak" herein) at time 506 and peak 508 at time 510. In the example shown, signal 502 may be a stimulation-evoked signal of a neural response of certain fibers of a nerve to electrical stimulation.

FIG. 6 is a plot 600 of another example stimulation-evoked signal 602, in accordance with one or more techniques of this disclosure. In the example shown, signal 602 is a voltage amplitude that varies in time in proportion to a time-varying electric field sensed by an electrode 232, the time-varying electric field caused by a signal source in response to electrical stimulation. In the example shown, signal 602 includes peak 604 at time 606. In the example shown, signal 602 may be a stimulation-evoked signal of an EMG of a muscle in response to electrical stimulation.

FIG. 7 is a plot 700 of another example stimulation-evoked signal 702, in accordance with one or more techniques of this disclosure. In the example shown, signal 702 is a voltage amplitude that varies in time in proportion to a time-varying electric field sensed by an electrode 232, the time-varying electric field caused by a signal source in response to electrical stimulation. In the example shown, signal 702 includes valley 704 at time 706. In the example shown, signal 702 may be a stimulation-evoked signal of a neural response of nerve fibers to electrical stimulation.

FIG. 8 is a plot 800 of another example stimulation-evoked signal 802, in accordance with one or more techniques of this disclosure. In the example shown, signal 802 is a voltage amplitude that varies in time in proportion to a time-varying electric field sensed by an electrode 232, the time-varying electric field caused by a signal source in response to electrical stimulation. In the example shown, signal 802 includes peak 804 at time 806. In the example shown, signal 802 may be a stimulation-evoked signal of a neural response of one or more fibers of a nerve or an EMG of a muscle in response to electrical stimulation.

FIG. 9 is a plot of an example composite stimulation-evoked signal, in accordance with one or more techniques of this disclosure. In the example shown, signal 902 is a voltage amplitude that varies in time in proportion to a time-varying electric field sensed by an electrode 232, the time-varying electric field caused by a plurality of signal sources in response to electrical stimulation. For example, signal 902 may be a composite of signals 502-802. Although not shown, signal 902 may include other peaks, features, artifacts, and/or noise. For example, electrode 232 may sense signal 902 but not signals 502-802, which are illustrated for as individual components of composite signal 902 for clarity.

In the example shown, composite stimulation-evoked signal 902 includes peaks 504, 508, 604, 704, 804, and 904 and 908 occurring at times 506, 510, 606, 706, 806, and 906 and 910, respectively. In the example shown, peak 904 may correspond to a combination of two or more signal sources. In other words, peak 904 may not be a peak caused by a signal source, but rather is a result of the combination of signals 502 and 702. Peak 908 may be a stimulation-evoked signal of an EMG of a muscle in response to electrical stimulation, e.g., a second contraction of the same muscle of peak 604 or a different muscle.

In some examples, a plurality of features of signal 902 may be determined, e.g., per (406) of the method illustrated and described above with reference to FIG. 4B. For example, IMD 200A, external programmer 300, or another device such as a computing device, may determine receive signal 902 and determine one or peaks 504, 508, 604, 704, 804, 904 and 908, the corresponding times of the peaks, latency between one or more peaks such as DT between peak 508 and 604, the widths and areas of any of the above peaks, the frequency and/or spectral content of signal 902, or any other signal feature, e.g., derivable via signal processing and/or digital signal processing.

In some examples, one or more determined feature may correspond to, and may be correlated with, the efficacy of stimulation therapy. For example, composite signals may be detected when the patient or patient population are experiencing, e.g. positive effects of treatment or negative effects of treatment, or no change with therapy and the detected composite signal can be used as an indicator or baseline of such treatment effects.

For example, peak 504 may relate to an electrical stimulation response of certain fibers of a nerve to electrical stimulation, peak 604 may relate to an EMG of a muscle, and peak 704 may relate to an electrical stimulation response of nerve fibers, e.g., which may relate to sensory and motor information. In some examples, improved and or optimal electrical stimulation therapy may be electrical stimulation that excites certain nerve fibers while reducing/minimizing excitation of certain other nerve fibers, e.g., such that peak 508 is increased and peak 704 is decreased. For example, a system may determine that leads 230 may be moved and/or stimulation parameters settings 242 may be adjusted to increase peak 508 (e.g., increase excitation of the certain nerve fibers) while also decreasing peak 704 (e.g., reducing valley 704 or making peak 704 less negative, representing a decrease of the excitation of certain other nerve fibers).

As another example, improved and or optimal electrical stimulation therapy may be electrical stimulation that reduces/minimizes fiber excitation of some fibers while increasing excitation of other nerve fibers and muscle contraction, e.g., the EMG response of a muscle. For example, a system may determine that leads 230 may be moved and/or stimulation parameters settings 242 may be adjusted to increase peak 704 (e.g., increase valley 704 or make peak 704 more negative, representing an increase of the excitation of certain fibers of a nerve) while increasing peak 604 (e.g., increasing the response and corresponding EMG of a muscle) and decreasing peak 508 (e.g., decreasing excitation of other fibers of a nerve).

EXAMPLES

Figure 10:
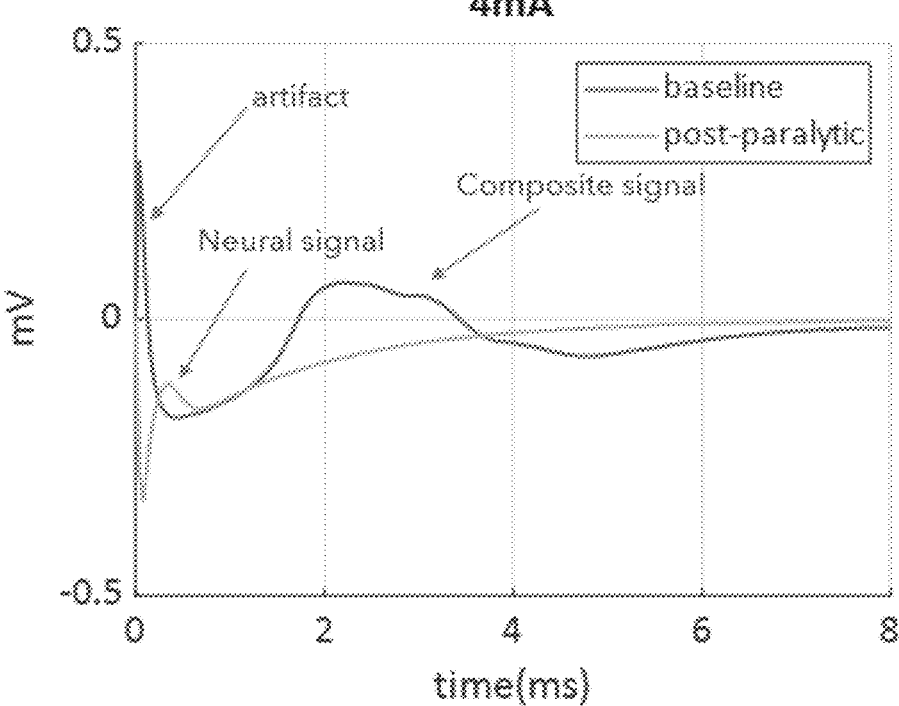
FIG. 10 illustrates a composite stimulation-evoked signal and a neural signal, in accordance with one or more techniques of this disclosure.

FIG. 10 illustrates a composite signal including two or more signals from one or more sources. As shown in FIG. 10, signals before (baseline) and after application of a systemic paralytic (to block muscle response) were sensed in response to stimulation with ranges of 0.5-100 Hz, 1-450 µs, 0.1-15 mA with recordings averaged over 2-500 traces. es. The baseline signal represents the composite signal in response to the stimulation, and includes a composite of neural (e.g. ECAP) and EMG signals. When the muscle activity was blocked (e.g. not able to contract), the EMG was removed from the composite signal, leaving only ECAP signal. FIG. 10 thus illustrates that the composite signal includes at least a neural signal and a muscle signal. The composite signal may be used in accordance of methods and systems of this disclosure, with or without identifying the individual signal sources. In other words, the composite signal itself may be of clinical significance. FIG. 11A-11C illustrate composite signals obtained from stimulation with ranges of 0.5-100 Hz, 1-450 μs, 0.1-15 mA with recordings averaged over 2-500 traces. For example, stimulation can be delivered at standard therapy of 210 μs, 14 Hz in a single subject at multiple configurations for sensing and stimulation electrodes from a lead. In FIG. 11A, the composite signal was obtained by simulating with A, D electrodes and sensing with B, C electrodes. In FIG. 11B, the composite signal was obtained by stimulating with B, C electrodes and sensing with A, D electrodes. In FIG. 11C, the composite signal was obtained by stimulating with A, C electrodes, and sensing with B, D electrodes. As indicated in FIGS. 11A-11C, the different composite signals were evoked by different stimulation configurations, and features from the different composite signals can be used in accordance with aspects of this disclosures, including but not limited to: assess, for example but not limited to, efficacy of response to stimulation, determine or adjust stimulation settings (e.g. stimulation parameters, timing, lead activation); determine or adjust stimulation therapy (e.g., timing and duration of stimulation), lead placement and efficacy (e.g. positioning or repositioning during trial stimulation (external/implant) or chronic implantation). For example, the quantity of the composite signals in FIGS. 11A-11C may indicate that positioning of the stimulations of the electrodes to elicit the response indicates positioning is sufficient to elicit therapeutic response, positioning is inconclusive, or positioning is insufficient to elicit therapeutic response. Alternatively, by varying stimulation settings (e.g. frequency, amplitude, duration) for the stimulation configurations in FIGS. 11A-11C and assessing the received composite signals from the varied stimulations settings, the composite signals may be used to identify which simulation settings of the varied stimulation settings are sufficient to elicit a therapeutic response, insufficient to determine therapeutic response, insufficient to elicit a therapeutic response.

The foregoing examples are not limiting, and the concepts described throughout the disclosure may be applied to the detected composite signal can more be used to more accurately or more reliably assess, for example but not limited to, efficacy of response to stimulation, determine or adjust stimulation settings (e.g. stimulation parameters, timing, lead activation); determine or adjust stimulation therapy (e.g., timing and duration of stimulation), lead placement and efficacy (e.g. positioning or repositioning during trial stimulation (external/implant) or chronic implantation).

The following numbered examples may illustrate one or more aspects of this disclosure:

Example 1: A method includes delivering one or more electrical stimulation signals to a patient; sensing a composite stimulation-evoked signal comprising a composite of signals generated by two or more signal sources in response to the one or more electrical stimulation signals; and controlling delivery of electrical stimulation therapy to the patient based on the composite stimulation-evoked signal.

Example 2: The method of example 1, wherein the two or more signal sources comprise two or more muscles of the patient.

Example 3: The method of any of examples 1 and 2, wherein the two or more signal sources comprise two or more nerves of the patient.

Example 4: The method of any of examples 1 through 3, wherein the two or more signal sources comprise at least one muscle and at least one nerve of the patient.

Example 5: The method of any one of examples 1-2, wherein the composite stimulation-evoked signal comprises a composite electromyographic (EMG) signal.

Example 6: The method of any one of examples 1-5, wherein at least one of the two or more signal sources are located at least 10 millimeters from a sensor sensing the composite stimulation-evoked signal.

Example 7: The method of any one of examples 1-6, wherein the composite stimulation-evoked signal has a duration of at least 5 milliseconds or at least 3 milliseconds.

Example 8: The method of any one of examples 1-7, wherein the one or more electrical stimulation signals are delivered to at least one sacral nerve of the patient.

Example 9: The method of any one of examples 1-8, wherein controlling therapy delivery comprises one or more: adjusting lead placement; adjusting therapy parameters; adjusting timing of therapy delivery; and determining whether the therapy is effective, and bypassing changes to therapy based on the determination that therapy is effective.

Example 10: The method of any one of examples 1-9, wherein sensing the composite stimulation-evoked signal comprises sensing the composite stimulation-evoked signal after: delivery of every electrical stimulation signal; delivery of a set number of electrical stimulation signals; or a set amount of time.

Example 11: The method of any one of examples 1-10, wherein delivering the one or more electrical stimulation signals to the patient comprises delivering the one or more electrical stimulation signals having one or more of non-equal pulse amplitudes, non-equal pulse durations, non-equal polarity, or non-equal pulse frequencies.

Example 12: The method of any one of examples 1-11, further includes determining one or more features of the composite stimulation-evoked signal; and determining one or more classifications of the one or more features, wherein controlling therapy delivery to the patient is based on the one or more classifications.

Example 13: The method of example 12, wherein determining one or more features of the composite stimulation-evoked signal is based on a trained machine learning model.

Example 14: The method of any one of examples 1-13, wherein the composite stimulation-evoked signal comprises an evoked compound action potential (ECAP) and another signal.

Example 15: The method of any one of examples 1-14, wherein the composite stimulation-evoked signal comprises an EMG and another signal.

Example 16: The method of any one of examples 1-15, wherein an amplitude of a peak of the composite stimulation-evoked signal is greater than 0.001 millivolt, 0.01 millivolt, greater than 0.1 mV or greater than 1 mV.

Example 17: A system includes at least one electrode configured to deliver the electrical stimulation to a patient; and a device including processing circuitry configured to: deliver one or more electrical stimulation signal to the patient; sense a composite stimulation-evoked signal including a composite of electrical signals generated by two or more signal sources in response to the one or more electrical stimulation signals; and control delivery of electrical stimulation therapy to the patient based on the composite stimulation-evoked signal.

Example 18: The system of example 17, wherein the two or more signal sources comprise two or more muscles of the patient.

Example 19: The system of any of examples 17 and 18, wherein the two or more signal sources comprise two or more nerves of the patient.

Example 20: The system of any of examples 17 through 19, wherein the two or more signal sources comprise at least one muscle and at least one nerve of the patient.

Example 21: The system of any one of examples 17-18, wherein the composite stimulation-evoked signal comprises a composite electromyographic (EMG) signal.

Example 22: The system of any one of examples 17-21, wherein at least one of the two or more signal sources are located at least 10 millimeters from a sensor sensing the composite stimulation-evoked signal.

Example 23: The system of any one of examples 17-22, wherein the composite stimulation-evoked signal has a duration of at least 5 milliseconds.

Example 24: The system of any one of examples 17-23, wherein the one or more electrical stimulation signals are delivered to at least one sacral nerve of the patient.

Example 25: The system of any one of examples 17-24, wherein controlling therapy delivery comprises one or more: adjusting lead placement; adjusting therapy parameters; adjusting timing of therapy delivery; and determining whether the therapy is effective, and bypassing changes to therapy based on the determination that therapy is effective.

Example 26: The system of any one of examples 17-25, wherein sensing the composite stimulation-evoked signal comprises sensing the composite stimulation-evoked signal after: delivery of every electrical stimulation signal; delivery of a set number of electrical stimulation signals; or a set amount of time.

Example 27: The system of any one of examples 17-26, wherein the processing circuitry is further configured to: determine one or more features of the composite stimulation-evoked signal; and determine one or more classifications of the one or more features, wherein controlling therapy delivery to the patient is based on the one or more classifications.

Example 28: The system of example 27, wherein determining one or more features of the composite stimulation-evoked signal is based on a trained machine learning model.

Example 29: The system of any one of examples 17-28, wherein the composite stimulation-evoked signal comprises an evoked compound action potential (ECAP) and another signal.

Example 30: The system of any one of examples 17-29, wherein the composite stimulation-evoked signal comprises a compound muscle action potential (CMAP) and another signal.

Example 31: The system of any one of examples 17-30, wherein an amplitude of a peak of the composite stimulation-evoked signal is greater than 1 millivolt.

Example 32: A computer readable medium includes instructions that when executed cause one or more processors to: deliver one or more electrical stimulation signals to a patient; sense a composite stimulation-evoked signal comprising a composite of signals generated by two or more signal sources in response to the one or more electrical stimulation signals; and control delivery of electrical stimulation therapy to the patient based on the composite stimulation-evoked signal. Example 33: A method comprising delivering one or more electrical stimulation signals to a patient; sensing a composite stimulation-evoked signal comprising a composite of signals generated by one or more signal sources in response to the one or more electrical stimulation signals; and controlling delivery of electrical stimulation therapy to the patient based on the composite stimulation-evoked signal.

Example 34: A system comprising: at least one electrode configured to deliver the electrical stimulation to a patient; and a device comprising processing circuitry configured to: deliver one or more electrical stimulation signal to the patient; sense a composite stimulation-evoked signal comprising a composite of electrical signals generated by one or more signal sources in response to the one or more electrical stimulation signals; and control delivery of electrical stimulation therapy to the patient based on the composite stimulation-evoked signal.

The techniques described in this disclosure may be implemented, at least in part, in hardware, software, firmware or any combination thereof. For example, various aspects of the described techniques may be implemented within processing circuitry, which may include one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit including hardware may also form one or more processors or processing circuitry configured to perform one or more of the techniques of this disclosure.

Such hardware, software, and firmware may be implemented, and various operation may be performed within same device, within separate devices, and/or on a coordinated basis within, among or across several devices, to support the various operations and functions described in this disclosure. In addition, any of the described units, circuits or components may be implemented together or separately as discrete but interoperable logic devices. Depiction of different features as circuits or units is intended to highlight different functional aspects and does not necessarily imply that such circuits or units must be realized by separate hardware or software components. Rather, functionality associated with one or more circuits or units may be performed by separate hardware or software components or integrated within common or separate hardware or software components. Processing circuitry described in this disclosure, including a processor or multiple processors, may be implemented, in various examples, as fixed-function circuits, programmable circuits, or a combination thereof. Fixed-function circuits refer to circuits that provide particular functionality with preset operations. Programmable circuits refer to circuits that can be programmed to perform various tasks and provide flexible functionality in the operations that can be performed. For instance, programmable circuits may execute software or firmware that cause the programmable circuits to operate in the manner defined by instructions of the software or firmware. Fixed-function circuits may execute software instructions (e.g., to receive stimulation parameters or output stimulation parameters), but the types of operations that the fixed-function circuits perform are generally immutable. In some examples, one or more of the units may be distinct circuit blocks (fixed-function or programmable), and in some examples, one or more of the units may be integrated circuits.

The techniques described in this disclosure may also be embodied or encoded in a computer-readable medium, such as a computer-readable storage medium, containing instructions that may be described as non-transitory media. Instructions embedded or encoded in a computer-readable storage medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

What is claimed is:

1. A method comprising:

delivering one or more electrical stimulation signals to a patient to activate a plurality of muscles;

sensing a single composite stimulation-evoked signal comprising a composite of a plurality of electromyographic (EMG) signals evoked from the one or more electrical stimulation signals activating the plurality of muscles; and controlling delivery of electrical stimulation therapy to the patient based on the single composite stimulation-evoked signal.

2. The method of claim 1, wherein the single composite stimulation-evoked signal further comprises a plurality of evoked compound action potential (ECAP) signals evoked from stimulating a plurality of nerves of the patient.

3. The method of claim 1, wherein at least one of the plurality of muscles is located at least 10 millimeters from a sensor sensing the single composite stimulation-evoked signal.

4. The method of claim 1, wherein the single composite stimulation-evoked signal has a duration of at least 2 milliseconds.

5. The method of claim 1, wherein the one or more electrical stimulation signals are delivered to at least one sacral nerve of the patient.

6. The method of claim 1, wherein controlling delivery comprises one or more:

adjusting lead placement;

adjusting therapy parameters;

adjusting timing of therapy delivery;

determining whether the therapy is consistent;

determining whether the therapy is effective, and bypassing changes to therapy based on the determination that therapy is effective.

7. The method of claim 1, wherein sensing the single composite stimulation-evoked signal comprises sensing the single composite stimulation-evoked signal after:

delivery of every electrical stimulation signal;

delivery of a set number of electrical stimulation signals; or a set amount of time.

8. The method of claim 1, wherein delivering the one or more electrical stimulation signals to the patient comprises delivering the one or more electrical stimulation signals having one or more of non-equal pulse amplitudes, non-equal pulse durations, non-equal pulse polarity or non-equal pulse frequencies.

9. The method of claim 1, further comprising:

determining one or more features of the single composite stimulation-evoked signal; and determining one or more classifications of the one or more features, wherein controlling therapy delivery to the patient is based on the one or more classifications.

10. The method of claim 9, wherein determining one or more features of the single composite stimulation-evoked signal is based on a trained machine learning model.

11. The method of claim 10, wherein the single composite stimulation-evoked signal further comprises an evoked compound action potential (ECAP) and another signal.

12. The method of claim 10, wherein an amplitude of a peak of the single composite stimulation-evoked signal is greater than at least one of 1 millivolt (mV), 0.1 mV, or 0.01 mV or 0.001 mV.

13. The method of claim 1, wherein the plurality of EMG signals are evoked from the same electrical stimulation signal of the one or more electrical stimulation signals.

14. The method of claim 13, wherein the plurality of EMG signals are combined as a function of time to form the single composite stimulation-evoked signal.

15. The method of claim 1, wherein the plurality of EMG signals add to form the single composite stimulation-evoked signal that is sensed.

16. The method of claim 1, wherein the plurality of EMG signals form the single composite stimulation-evoked signal that is then sensed.

17. The method of claim 1, wherein delivering the one or more electrical stimulation signals comprises delivering the one or more electrical stimulation signals to at least one pudendal nerve of the patient to activate the plurality of muscles.

18. A system comprising:

at least one electrode configured to deliver electrical stimulation to a patient; and a device comprising processing circuitry configured to:

deliver one or more electrical stimulation signals to the patient to activate a plurality of muscles;

sense a single composite stimulation-evoked signal comprising a composite of a plurality of electromyographic (EMG) signals evoked from the one or more electrical stimulation signals activating the plurality of muscles; and control delivery of electrical stimulation therapy to the patient based on the single composite stimulation-evoked signal.

19. The system of claim 18, wherein the single composite stimulation-evoked signal further comprises a plurality of evoked compound action potential (ECAP) signals evoked from stimulating a plurality of nerves of the patient.

20. The system of claim 18, wherein at least one of the plurality of muscles is located at least 10 millimeters from a sensor sensing the single composite stimulation-evoked signal.

21. The system of claim 17, wherein the plurality of EMG signals are evoked from the same electrical stimulation signal of the one or more electrical stimulation signals.

22. The system of claim 21, wherein the plurality of EMG signals are combined as a function of time to form the single composite stimulation-evoked signal.

23. The system of claim 18, wherein the at least one electrode is configured to deliver the electrical stimulation to at least one pudendal nerve of the patient, and wherein the processing circuitry is configured to deliver the one or more electrical stimulation signals to the at least one pudendal nerve of the patient to activate the plurality of muscles.

* * * * *